US010668294B2

(12) United States Patent
Koop et al.

(10) Patent No.: US 10,668,294 B2
(45) Date of Patent: Jun. 2, 2020

(54) LEADLESS CARDIAC PACEMAKER CONFIGURED FOR OVER THE WIRE DELIVERY

(71) Applicant: CARDIAC PACEMAKERS, INC., St. Paul, MN (US)

(72) Inventors: Brendan Early Koop, Ham Lake, MN (US); Benjamin J. Haasl, Forest Lake, MN (US); Brandon Christopher Fellows, Minneapolis, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 0 days.

(21) Appl. No.: 15/589,481

(22) Filed: May 8, 2017

(65) Prior Publication Data
US 2017/0326372 A1     Nov. 16, 2017

Related U.S. Application Data

(60) Provisional application No. 62/334,193, filed on May 10, 2016.

(51) Int. Cl.
*A61N 1/00* (2006.01)
*A61N 1/375* (2006.01)
(Continued)

(52) U.S. Cl.
CPC ......... *A61N 1/3756* (2013.01); *A61N 1/0573* (2013.01); *A61N 1/3684* (2013.01); *A61N 1/36843* (2017.08); *A61N 1/37518* (2017.08)

(58) Field of Classification Search
CPC .... A61N 1/3756; A61N 1/3684; A61N 1/372; A61N 1/37205; A61N 1/375; A61N 1/3968; A61N 1/0573
See application file for complete search history.

(56) References Cited

U.S. PATENT DOCUMENTS

| 3,835,864 A | 9/1974 | Rasor et al. |
| 3,943,936 A | 3/1976 | Rasor et al. |

(Continued)

FOREIGN PATENT DOCUMENTS

| AU | 2008279789 B2 | 10/2011 |
| AU | 2008329620 B2 | 5/2014 |

(Continued)

OTHER PUBLICATIONS

US 8,886,318 B2, 11/2014, Jacobson et al. (withdrawn)
(Continued)

*Primary Examiner* — Scott M. Getzow
(74) *Attorney, Agent, or Firm* — Seager, Tufte & Wickhem LLP

(57) ABSTRACT

Implantable medical devices such as leadless cardiac pacemakers (LCP) may be configured to be delivered to a target location within the heart over a guide wire. In some cases, using a guide wire for delivery facilitates placement of devices in regions not otherwise easily reached. An LCP may include a housing and a wire lumen disposed relative to the housing. The wire lumen may be configured to allow the LCP to slide over a guide wire. In some cases, the guide wire may include a guide wire electrode that may be used to test potential implantation sites.

20 Claims, 21 Drawing Sheets

(51) Int. Cl.
*A61N 1/05* (2006.01)
*A61N 1/368* (2006.01)

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | DePinto |
| 5,269,326 A | 12/1993 | Verrier |
| 5,284,136 A | 2/1994 | Hauck et al. |
| 5,300,107 A | 4/1994 | Stokes et al. |
| 5,300,108 A * | 4/1994 | Rebell ................ A61N 1/0573 607/127 |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | deCoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Rostami et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras, Sr. et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | DePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |

(56) References Cited

U.S. PATENT DOCUMENTS

| | | |
|---|---|---|
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |

(56) References Cited

U.S. PATENT DOCUMENTS

| | | |
|---|---|---|
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,321,798 B2 | 1/2008 | Muhlenberg et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,050,774 B2 | 11/2011 | Kveen et al. |

(56) References Cited

U.S. PATENT DOCUMENTS

| | | |
|---|---|---|
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,262,578 B1 | 9/2012 | Bharmi et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |

(56) References Cited

U.S. PATENT DOCUMENTS

| | | | |
|---|---|---|---|
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,731,138 B1* | 8/2017 | Stadler .......... A61B 5/0422 |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0230283 A1 | 11/2004 | Prinzen et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0043765 A1* | 2/2005 | Williams ............ A61N 1/057 607/9 |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |

(56) References Cited

U.S. PATENT DOCUMENTS

| | | |
|---|---|---|
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088395 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0088418 A1* | 4/2007 | Jacobson ............. A61N 1/3708 607/116 |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0294229 A1 | 11/2008 | Friedman et al. |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M. |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0069983 A1 | 3/2010 | Peacock, III et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0298841 A1 | 11/2010 | Prinzen et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1* | 11/2011 | Pellegrini ............ A61N 1/0573 607/9 |
| 2011/0270341 A1 | 11/2011 | Ruben et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |

(56) References Cited

U.S. PATENT DOCUMENTS

| | | |
|---|---|---|
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0245665 A1 | 9/2012 | Friedman et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0289776 A1 | 11/2012 | Keast et al. |
| 2012/0289815 A1 | 11/2012 | Keast et al. |
| 2012/0290021 A1 | 11/2012 | Saurkar et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1* | 5/2013 | Bornzin ............ A61N 1/36592 607/17 |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0192611 A1 | 8/2013 | Taepke, II et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253309 A1 | 9/2013 | Allan et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100624 A1 | 4/2014 | Ellingson |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222015 A1 | 8/2014 | Keast et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0343348 A1 | 11/2014 | Kaplan et al. |
| 2014/0371818 A1 | 12/2014 | Bond et al. |
| 2014/0378992 A1* | 12/2014 | Ollivier ............... A61N 1/0573 606/129 |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0045868 A1 | 2/2015 | Bonner et al. |

(56) References Cited

U.S. PATENT DOCUMENTS

| | | |
|---|---|---|
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0126854 A1 | 5/2015 | Keast et al. |
| 2015/0157861 A1 | 6/2015 | Aghassian |
| 2015/0157866 A1 | 6/2015 | Demmer et al. |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0230699 A1 | 8/2015 | Berul et al. |
| 2015/0238769 A1 | 8/2015 | Demmer et al. |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306401 A1 | 10/2015 | Demmer et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0335884 A1 | 11/2015 | Khairkhahan et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0279423 A1* | 9/2016 | Kelly ............... A61N 1/372 |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0304624 A1* | 10/2017 | Friedman ............... A61N 1/057 |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 2005000206 A2 | 1/2005 |
| WO | 2005042089 A1 | 5/2005 |
| WO | 2006065394 A1 | 6/2006 |
| WO | 2006086435 A2 | 8/2006 |
| WO | 2006113659 A1 | 10/2006 |
| WO | 2006124833 A2 | 11/2006 |
| WO | 2007073435 A1 | 6/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A2 | 7/2013 |
| WO | 2013184787 A1 | 12/2013 |
| WO | 2014120769 A1 | 8/2014 |

OTHER PUBLICATIONS

"Instructions for Use System 1, Leadless Cardiac Pacemaker (LCP) and Delivery Catheter," Nanostim Leadless Pacemakers, pp. 1-28, 2013.

Asirvatham et al., "Intramyocardial Pacing and Sensing for the Enhancement of Cardiac Stimulation and Sensing Specificity," PACE, vol. 30, pp. 748-754, Jun. 2007.

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Henz et al., "Synchronous Ventricular Pacing without Crossing the Tricuspid Valve or Entering the Coronary Sinus-Preliminary Results," Journal of Cardiovascular Electrophysiology, vol. 20(12):1391-1397, Dec. 2009.doi: 10.1111/j.1540-8167.2009.01556.x.

Hyde et al., Beneficial Effect on Cardiac Resynchronization From Left Ventricular Endocardial Pacing Is Mediated by Early Access to High Conduction Velocity Tissue Electrophysiological Simulation Study, Circ Arrhythm Electrophysiol, 8, 1164-1172, 2015, DOI: 10.1161/CIRCEP.115.002677.

Rad et al., Left ventricular septum pacing by transvenous approach through the interventricular septum, Maastricht University Medical Center.

Seyedi et al., "A Survey on Intrabody Communications for Body Area Network Application," IEEE Transactions on Biomedical Engineering, vol. 60(8): 2067-2079, 2013.

Spickler et al., "Totally Self-Contained Intracardiac Pacemaker," Journal of Electrocardiology, vol. 3(3&4): 324-331, 1970.

Wegmüller, "Intra-Body Communication for Biomedical Sensor Networks," Diss. ETH, No. 17323, 1-173, 2007.

* cited by examiner

LEADLESS CARDIAC PACEMAKER CONFIGURED FOR OVER THE WIRE DELIVERY

CROSS REFERENCE TO RELATED APPLICATIONS

This application claims the benefit of U.S. Provisional Patent Application Ser. No. 62/334,193 filed on May 10, 2016, the disclosure of which is incorporated herein by reference.

TECHNICAL FIELD

The disclosure relates generally to implantable medical devices, and more particularly to implantable medical devices such as leadless cardiac pacemakers.

BACKGROUND

Implantable medical devices are commonly used today to monitor a patient and/or deliver therapy to a patient. For example, implantable sensors are often used to monitor one or more physiological parameters of a patient, such as heart beats, heart sounds, ECG, respiration, etc. In another example, pacing devices are often used to treat patients suffering from various heart conditions that may result in a reduced ability of the heart to deliver sufficient amounts of blood to a patient's body. Such heart conditions may lead to slow, rapid, irregular, and/or inefficient heart contractions. To help alleviate some of these conditions, various medical devices (e.g., pacemakers, defibrillators, etc.) can be implanted in a patient's body. Such devices may monitor and in some cases provide electrical stimulation to the heart to help the heart operate in a more normal, efficient and/or safe manner. Under some circumstances, it can be beneficial to sense and/or pace two or more chambers of the heart.

SUMMARY

This disclosure relates generally to implantable medical devices, and relates more particularly to implantable medical devices such as leadless cardiac pacemakers. In some cases, an implantable medical device may be configured to be delivered to a target location within the heart over a guide wire. In some cases, using a guide wire for delivery facilitates placement of such implantable medical devices in regions that are not otherwise easily reached.

In an example of the disclosure, a leadless cardiac pacemaker (LCP) is configured for pacing a patient's heart from within a chamber of the patient's heart. The LCP may be configured for delivery to an implantation site within the patient's heart over an elongated guide wire. The illustrative LCP may include a housing that is configured to be positioned within the chamber of the patient's heart proximate a chamber wall once implanted. Circuitry may be disposed within the housing and operatively coupled to an internal power source. An electrode may be fixed relative to the housing and may be positioned to contact the chamber wall once the LCP is implanted. The circuitry may be configured to pace the patient's heart via the electrode. A wire lumen may be configured to permit the LCP to slide over an elongated guide wire to the implantation site. The illustrative LCP may further include a fixation element for extending into the chamber wall at the implantation site to fix the LCP relative to the chamber wall at the implantation site. The fixation element may be fixed to the LCP and delivered along with the LCP to the implantation site.

Alternatively or additionally to the illustrative embodiment above, the fixation element may be configured to engage the chamber wall once the LCP is at the implantation site and to fix the LCP relative to the chamber wall with the electrode of the LCP in contact with the chamber wall.

Alternatively or additionally to any of the embodiments above, the fixation element may include a helical screw.

Alternatively or additionally to any of the embodiments above, the helical screw may be secured relative to the housing via threads, and the helical screw may be advanced distally relative to the housing by rotating the helical screw relative to the housing.

Alternatively or additionally to any of the embodiments above, the helical screw may be rotated relative to the housing by an LCP pusher that is configured to push the LCP along the elongated guide wire and also rotate the helical screw relative to the housing.

Alternatively or additionally to any of the embodiments above, the fixation element may include one or more tines.

Alternatively or additionally to any of the embodiments above, the one or more tines may be configured to extend distally of the housing and bend outward. In some cases, the one or more tines may be confined by a LCP delivery sheath that extends over the LCP and the one or more tines while the LCP is delivered along the elongated guide wire to the implantation site. In some instances, the one or more tines may be configured to extend into the chamber wall and bend outward when the LCP is pushed out of the LCP delivery sheath at the implantation site.

Alternatively or additionally to any of the embodiments above, the wire lumen may extend concentrically through the LCP along a longitudinal axis of the LCP. In other instances, the LCP may further include a tubular structure secured relative to an outer surface of the housing, wherein the tubular structure forms the wire lumen.

Alternatively or additionally to any of the embodiments above, the electrode may be a right ventricle (RV) electrode, and the LCP may further include an LV electrode support extending distally away from the housing. In some cases, the LV electrode support may include two or more LV electrodes each spaced at a different distance distally from the housing. The two or more LV electrodes may be operatively coupled to the circuitry of the LCP and each may be independently selectable by the circuitry of the LCP. The circuitry may be configured to pace the right ventricle (RV) of the patient's heart via the RV electrode and to pace the left ventricle (LV) of the patient's heart via one or more of the LV electrodes.

In another example of the disclosure, a system for delivering a leadless cardiac pacemaker (LCP) to an implantation site within a chamber of a patient's heart is disclosed. The illustrative system may include an elongated guide wire configured to extend transvascularly to within the chamber of the patient's heart and to the implantation site. The elongated guide wire may include a guide wire electrode at or near its distal end that is usable to test suitability of the implantation site. The illustrative system may further include an LCP that has a housing configured to be positioned within the chamber of the patient's heart proximate a chamber wall once implanted. A power source may be disposed within the housing of the LCP. Circuitry may be disposed within the housing and may be operably coupled to the power source. One or more electrodes may be disposed relative to the housing and positioned to contact the chamber wall once the LCP has been implanted. The circuitry may be configured to pace the patient's heart via the one or more electrodes. The LCP may include a wire lumen configured to permit the LCP to slide over the elongated guide wire to the implantation site, and may further include a fixation element for extending into the chamber wall at the implantation site to fix the LCP relative to the chamber wall at the implantation site. In some cases, the fixation element may be fixed to the LCP and delivered along with the LCP to the implantation site.

Alternatively or additionally to any of the embodiments above, the elongated guide wire is configured to pierce at least partially through the chamber wall at the implantation site with at least part of or the entire guide wire electrode positioned inside of the chamber wall.

Alternatively or additionally to any of the embodiments above, the elongated guide wire may further includes a fixation element for fixing the elongated guide wire to the chamber wall.

Alternatively or additionally to the above embodiment, the fixation element of the elongated guide wire may include a fixation helix, and the guide wire electrode may be disposed proximate a distal end of the fixation helix.

Alternatively or additionally to any of the embodiments above, the wire lumen of the LCP may be configured to be engageable with the elongated guide wire in order to utilize the guide wire electrode of the elongated guide wire as one of the one or more electrodes of the LCP. In some cases, a proximal portion of the elongated guide wire extending proximally from the housing may be subsequently separatable from a distal portion of the guide wire and may be withdrawn from the patient's heart.

Alternatively or additionally to any of the embodiments above, the wire lumen of the LCP may be configured to frictionally engage the elongated guide wire in order to electrically couple and mechanically secure the LCP to the elongated guide wire during implantation.

Alternatively or additionally to any of the embodiments above, the wire lumen of the LCP may include a threaded section that is configured to engage a corresponding threaded section on the elongated guide wire in order to electrically couple and mechanically secure the LCP to the elongated guide wire during implantation.

In another example of the disclosure, a trans-septal implantable medical device (IMD) is configured for deployment within a patient's heart, adjacent a septum within the patient's heart, for pacing and/or sensing the patient's heart. The trans-septal IMD may be configured for delivery over an elongated guide wire and may include a housing that is configured to be positioned adjacent a first side of the septum once implanted. A power source may be disposed within the housing. Circuitry may be disposed within the housing and operably coupled to the power source. A first electrode may be disposed relative to the housing and positioned to contact the first side of the septum. A second electrode may be configured to extend from the housing and into or through the septum once the trans-septal IMD is implanted. The circuitry may be configured to pace the patient's heart and/or sense electrical activity of the patient's heart via the first electrode and the second electrode, and in some cases, may be configured to separately pace and/or sense each of two or more the heart chambers defined by the septum. The septum may be, for example, the ventricle-ventricle septum separating the right and left ventricle chambers, the atrial-atrial septum separating the right and left atrial chambers, or the atrium-ventricle septum separating the right atrial and the left ventricle chambers. The housing may define a wire lumen that is configured to permit the trans-septal IMD to be delivered to a position proximate the septum over an elongated guide wire. A fixation element may be operable to fixate the trans-septal IMD relative to the septum. In some cases, the fixation element may be fixed to the LCP and delivered along with the LCP to the implantation site, but this is not required.

The above summary is not intended to describe each and every disclosed embodiment or every implementation of the present disclosure. The Figures and Description which follow more particularly exemplify these and other illustrative embodiments.

BRIEF DESCRIPTION OF THE FIGURES

The disclosure may be more completely understood in consideration of the following description in connection with the accompanying drawings, in which.

Figure 1:
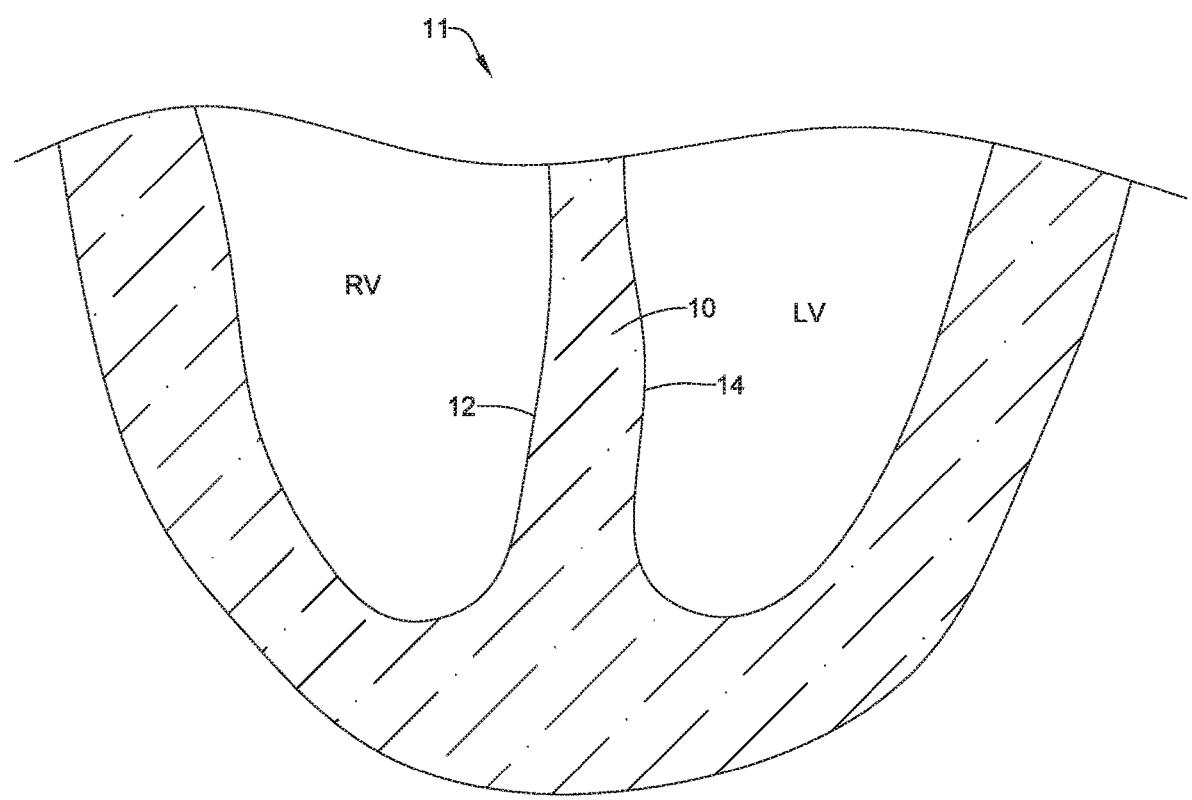
FIG. 1 is a schematic illustration of the lower portion of a human heart, referencing a right ventricle (RV), a left ventricle (LV) and the ventricular septum therebetween.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following description should be read with reference to the drawings in which similar structures in different drawings are numbered the same. The drawings, which are not necessarily to scale, depict illustrative embodiments and are not intended to limit the scope of the disclosure.

FIG. 1 is a schematic illustration of a lower portion of a human heart H. The heart H includes an RV (right ventricle) and an LV (left ventricle). A ventricular septum 10 separates the RV and the LV. While the heart H also includes, for example, an atrial septum between the right atrium and the left atrium, and an atrioventricular septum between the right atrium and the left ventricular, for simplicity the conversation is centered on the ventricular septum 10. The ventricular septum 10 may be considered as having an RV facing side 12 and an LV facing side 14.

It is known that the ventricular septum 10 includes conduction pathways that are involved in causing contractions in the RV and the LV. In some cases, reaching the RV through the vasculature, such as through the superior vena cava or the inferior vena cava and through the right atrium (not illustrated), may be easier than reaching the LV in an intravascular approach. In some cases, debris may be formed within the heart H as a result of placing and manipulating implantable devices within the heart H. In some cases, debris within the RV may be less problematic for the patient than debris within the LV, as debris within the RV may pass into the patient's lungs which can act as a filter while potential debris within the LV may pass directly into the patient's brain, potentially causing a stroke or other complications. Moreover, in some cases, the presence of a significant foreign object (e.g. an implantable medical device) within the heart H may cause tissue ingrowth and/or clotting to occur as a result of the body's natural response to the presence of the foreign body. Such clots, if released, are less of a concern in the RV than the LV.

In some instances, an Implantable Medical Device (IMD) such as, but not limited to, a Leadless Cardiac Pacemaker (LCP) may be configured to be deployed within the RV, next to or proximate the RV facing side 12 of the ventricular septum 10. A portion of the IMD or LCP may, for example, extend partially into the ventricular septum 10, or even completely through the ventricular septum 10, in order to place one or more electrodes in position to capture the aforementioned conduction pathways through the ventricular septum 10 that control the contraction of the LV, or to otherwise sense or pace within the LV. It will be appreciated that in some cases, the portion or portions of the IMD or LCP that penetrate into the LV may be minimized in size in order to minimize the body's natural response to such a foreign body. In some cases, the portion or portions of the IMD or LCP that penetrate into the LV, and in some instances even the portion or portions of the IMD or LCP that remain within the RV, may be coated with or otherwise include one or more anticoagulant materials.

Figure 2:
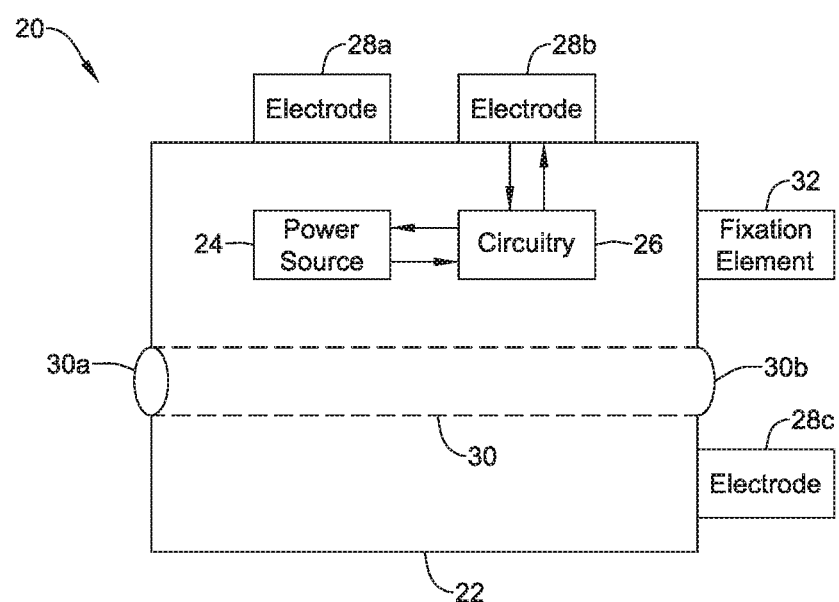
FIG. 2 is a schematic diagram of an illustrative implantable medical device (IMD) that may be delivered over a wire and disposed relative to the ventricular septum or other septum of a patient's heart.

FIG. 2 is a highly schematic diagram of an illustrative IMD 20 that may be utilized within the heart H. In some cases, the IMD 20 may be configured to be deployed proximate the RV facing side 12 of the ventricular septum 10, but this is merely illustrative. In some cases, the IMD 20 may include a housing 22 that is configured to be disposed at least partially within the RV, next to or proximate the RV facing side 12 of the ventricular septum 10, for example. A power source 24 may be disposed within the housing 22. In some cases, the power source 24 may be a battery. In some instances, the power source 24 may be a rechargeable power source, such as a rechargeable battery, a capacitor such as a super-capacitor and/or any other suitable rechargeable power source. Circuitry 26 may be disposed within the housing 22 and may be operatively coupled to the power source 24 such that the power source 24 can power operation of the circuitry 26. In some cases, if the power source 24 is rechargeable, the circuitry 26 may also regulate recharging operations of the power source 24. In some cases, the circuitry 26 may include or be coupled to an antenna, inductive loop and/or other energy receiving element for wirelessly receiving energy to recharge the battery.

The circuitry 26 may be operably coupled with one or more electrodes that are configured to provide pacing pulses to cardiac tissue and/or to sense electrical activity within the cardiac tissue. In some cases, for example, the IMD 20 may include two or more of electrode 28a, an electrode 28b and/or an electrode 28c. In some cases, the IMD 20 may include additional electrodes. In some cases, one or more of the electrodes 28a, 28b, 28c may be disposed relative to the housing 22 such that one or more of the electrodes 28a, 28b, 28c may contact tissue, such as but not limited to the RV facing side 12 of the ventricular septum 10 (FIG. 1) and thus may function as an RV electrode. In some cases, one or more of the electrodes 28a, 28b, 28c may function as an anode, and one or more of the electrodes 28a, 28b, 28c may function as a cathode.

In the example shown, a wire lumen 30 extends through the housing or body 22 from a first lumen end 30a to a second lumen end 30b. The wire lumen 30 may be configured to permit the IMD 20 to be advanced over a guide wire. In some cases, the wire lumen 30 may pass through a center of the housing 22, as will be discussed for example with respect to FIG. 7. In some cases, the wire lumen 30 may be offset from the center or longitudinal axis of the housing 22. In some instances, the wire lumen 30 may extend through a tube or other structure mounted to an exterior of the housing 22, as will be discussed for example with respect to FIG. 8.

In some cases, the IMD 20 may be configured to engage the guide wire in order to secure the IMD 20 in place relative to the guide wire. In some cases, for example, a distal portion of the guide wire may be used by the IMD 20 as an electrode after implantation. In one example, a threaded engagement may be used, as will be discussed in greater detail with respect to FIG. 14. A frictional engagement mechanism will be discussed in greater detail with respect to FIG. 15.

In some cases, as will be discussed, being able to deliver the IMD 20 over a guide wire may facilitate placement of the IMD 20 in particular locations within the heart H that may otherwise be difficult to reach via traditional delivery methods such as placing the IMD 20 in a distal cavity or sheath of a catheter-based delivery system. In some cases, as will be discussed, the guide wire itself may be configured to permit use of the guide wire in testing possible implantation sites for suitable capture and other desired electrical properties. For example, the guide wire may include one or more electrodes at or near its distal end. If more than one electrode is provided, each electrode may be separately addressable. Such electrode(s) may be used, for example, to test various locations on the chamber wall (such as but not limited to the ventricular septum 10 (FIG. 1)) capture and other desired electrical properties. In some cases, particularly if there are multiple addressable electrodes disposed at different spaced locations along the length of the distal end of the guide wire, the addressable electrodes may be used to test for capture and other properties at different depths within the ventricular septum 10, including the capture threshold of the LV.

The illustrative IMD 20 includes a fixation element 32 that may be configured to extend into a heart chamber wall in order to secure the IMD 20 relative to the chamber wall at a desired implantation site. The fixation element 32 is fixed or secured to the IMD 20, and in some cases is delivered to the implantation site with the IMD 20. In some instances, the fixation element 32 may be configured to engage the chamber wall (such as the ventricular septum 10) once the IMD 20 is at the implantation site, and to fix the IMD 20 relative to the chamber wall with one or more of the electrodes 28a, 28b, 28c (or others) in contact with the chamber wall.

In some cases, the fixation element 32 may include one or more tines that are configured to extend distally from the IMD 20 and engage cardiac tissue. In some cases, the tines may be movable between a straight configuration for delivery and extending into the cardiac tissue and a curved or hooked configuration for securing the IMD 20 relative to the cardiac tissue, as will be discussed further with respect to FIGS. 10 and 11. In some cases, the fixation element 32 includes a helical screw, as will be discussed further with respect to FIGS. 9 and 13.

Figure 3:
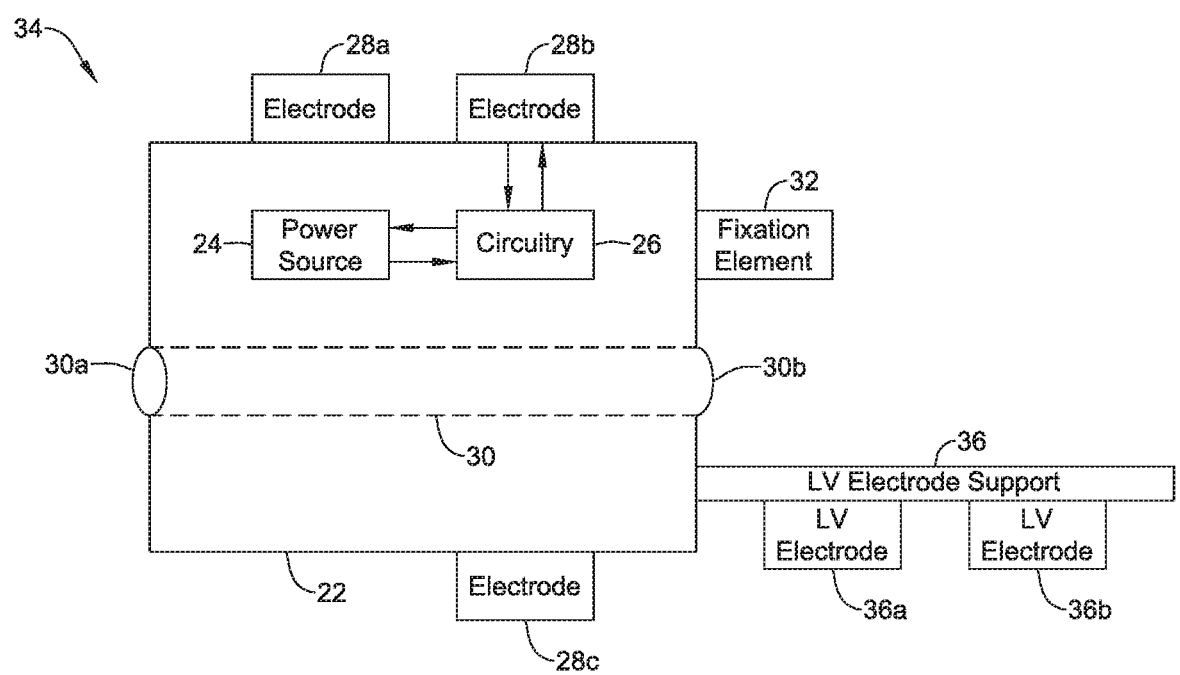
FIG. 3 is a schematic diagram of an illustrative IMD that may be delivered over a wire and disposed relative to the ventricular or other septum with a portion of the IMD penetrating into the ventricular or other septum.

FIG. 3 is a highly schematic diagram of an illustrative IMD 34 that may be utilized within the heart H. In some cases, the IMD 34 may be configured to be deployed proximate the RV facing side 12 of the ventricular septum 10, but this is merely illustrative. In some cases, the IMD 34 may include a housing 22 that is configured to be disposed at least partially within the RV, next to or proximate the RV facing side 12 of the ventricular septum 10, for example. The IMD 34 may be similar in structure to the IMD 20 (FIG. 2), but further includes an LV electrode support 36 that extends distally from the housing 22, and in some cases, may be configured to extend into and/or through the ventricular septum 10 (FIG. 1) in order to reach at or near the LV facing side 14 of the ventricular septum 10.

Figure 4:
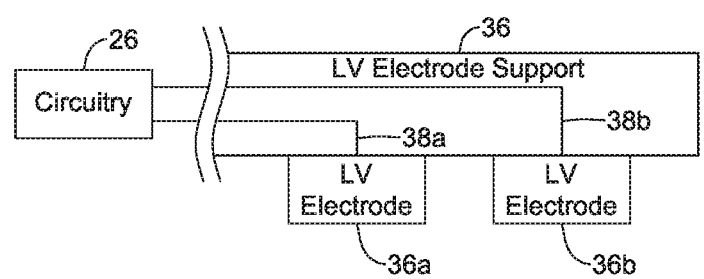
FIG. 4 is an enlarged view of the LV electrode support of the IMD of FIG. 3.

In the example shown, the LV electrode support 36 may include an LV electrode 36a and an LV electrode 36b. In some cases, there may only be one LV electrode. In some cases, there may be additional LV electrodes. In some cases, the LV electrodes 36a, 36b are individually addressable by the circuitry 26 and may, in some cases, be spaced at different distances distally from the housing 22. The LV electrodes 36a, 36b may be positioned relative to the LV electrode support 36 to place one or both of the LV electrodes 36a, 36b within the ventricular septum 10. In some cases, the LV electrodes 36a, 36b may be positioned relative to the LV electrode support 36 to place one or both of the LV electrodes 36a, 36b on the LV facing side 14 of the ventricular septum 10. In some cases, the LV electrode 36a and the LV electrode 36b are operably coupled with the circuitry 26. In some cases, as shown for example in FIG. 4, an electrical connection 38a extends from the LV electrode 36a to the circuitry 26, and an electrical connection 38b extends from the LV electrode 36b to the circuitry 26. It will be appreciated that one or more of the electrodes 28a, 28b, 28c may function as an RV electrode. In some cases, the circuitry 26 may pace the right ventricle RV of the heart H via one or more of the electrodes 28a, 28b, 28c, and may pace the left ventricle LV of the heart H via one or more of the LV electrodes 36a, 36b.

Figure 5:
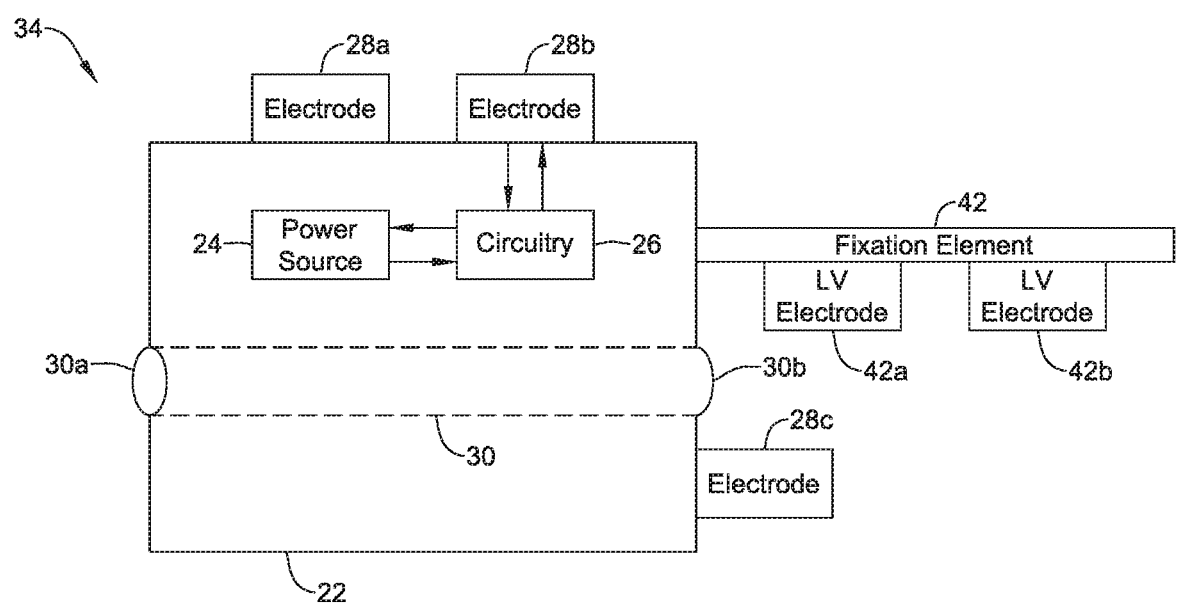
FIG. 5 is a schematic diagram of an illustrative IMD that may be delivered over a guide wire and disposed relative to the ventricular or other septum with a portion of the IMD penetrating into the ventricular or other septum.

FIG. 5 is a highly schematic diagram of an illustrative IMD 40 that may be utilized within the heart H. In some cases, the IMD 40 may be configured to be deployed proximate the RV facing side 12 of the ventricular septum 10, but this is merely illustrative. In some cases, the IMD 40 may include a housing 22 that is configured to be disposed at least partially within the RV, next to or proximate the RV facing side 12 of the ventricular septum 10, for example. The IMD 34 may be similar in structure to the IMD 20 (FIG. 2), but includes a fixation element 42 that extends distally from the housing 22 and that may be configured to extend into and/or through the ventricular septum 10 (FIG. 1) in order to anchor the IMD 40 as well as to reach at or near the LV facing side 14 of the ventricular septum 10. In some cases, as illustrated, the fixation element 42 may include one or more LV electrodes.

Figure 6:
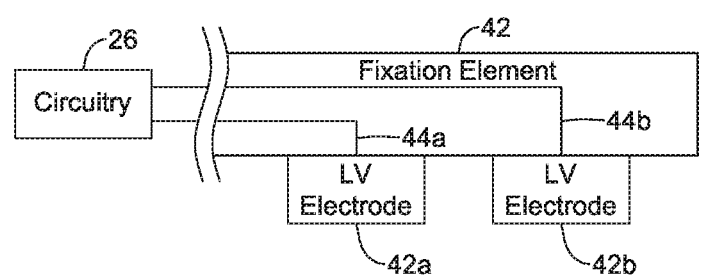
FIG. 6 is an enlarged view of the fixation element of the IMD of FIG. 5.

In FIG. 5, the fixation element 42 may include an LV electrode 42a and an LV electrode 42b. In some cases, there may only be one LV electrode. In some cases there may be additional LV electrodes. In some cases, the LV electrodes 42a, 42b may be individually addressable by the circuitry 26 and may, in some cases, be spaced different distances distally from the housing 22. The LV electrodes 42a, 42b may be positioned relative to the fixation element 42 to place one or both of the LV electrodes 42a, 42b within the ventricular septum 10. In some cases, the LV electrodes 42a, 42b may be positioned relative to the fixation element 42 to place one or both of the LV electrodes 42a, 42b on the LV facing side 14 of the ventricular septum 10. In some cases, the LV electrode 42a and the LV electrode 42b are operably coupled with the circuitry 26. In some cases, as shown for example in FIG. 6, an electrical connection 44a may extend from the LV electrode 42*a* to the circuitry 26 and an electrical connection 44*b* may extend from the LV electrode 42*b* to the circuitry 26. It will be appreciated that one or more of the electrodes 28*a*, 28*b*, 28*c* may function as an RV electrode. In some cases, the circuitry 26 may pace the right ventricle RV of the heart H via one or more of the electrodes 28*a*, 28*b*, 28*c*, and may pace the left ventricle LV of the heart H via one or more of the LV electrodes 42*a*, 42*b*.

Figure 7:
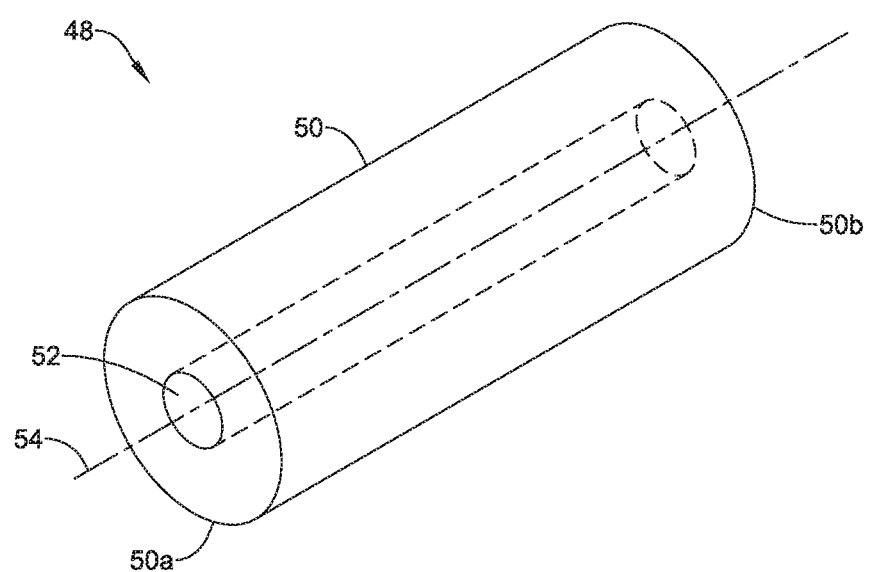
FIG. 7 is a schematic diagram of an illustrative IMD housing that may be delivered over a guide wire.
Figure 8:
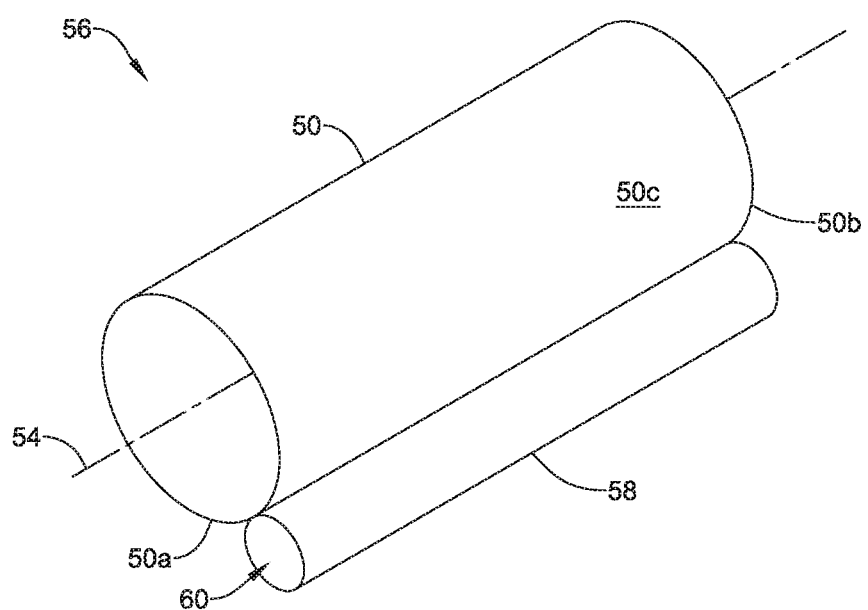
FIG. 8 is a schematic diagram of another illustrative IMD housing that may be delivered over a guide wire.

As referenced above, a wire lumen 30 may extend through the housing 22. The wire lumen 30 may take a variety of forms. For example, FIG. 7 shows an IMD 48 including a housing 50 that extends from a first end 50*a* to a second end 50*b*. A wire lumen 52 is shown extending through the housing 50 from the first end 50*a* to the second end 50*b*. In some cases, as illustrated, the wire lumen 52 is concentric with the housing 50, and the wire lumen 52 traverses along a longitudinal axis 54 of the housing 50. In other cases, the wire lumen 52 may be parallel with the longitudinal axis 54 but radially offset from the longitudinal axis 54. In some cases, as shown in FIG. 8 for example, an IMD 56 may include a tubular structure 58 that is secured to an outer surface 50*c* of the housing 50. As illustrated, the tubular structure 58 extends from the first end 50*a* to the second end 50*b* of the housing 50. In some cases, the tubular structure 58 may be shorter or longer than the length of the housing 50. The tubular structure 58 defines a wire lumen 60 for receiving a guide wire.

Figure 9:
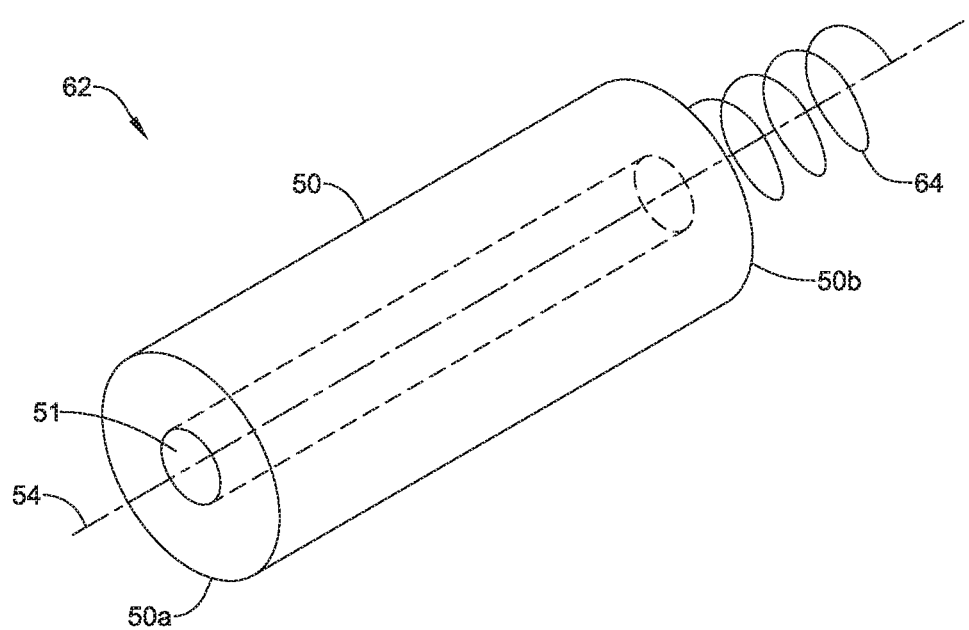
FIG. 9 is a schematic diagram of another illustrative IMD housing that may be delivered over a guide wire.
Figure 13:
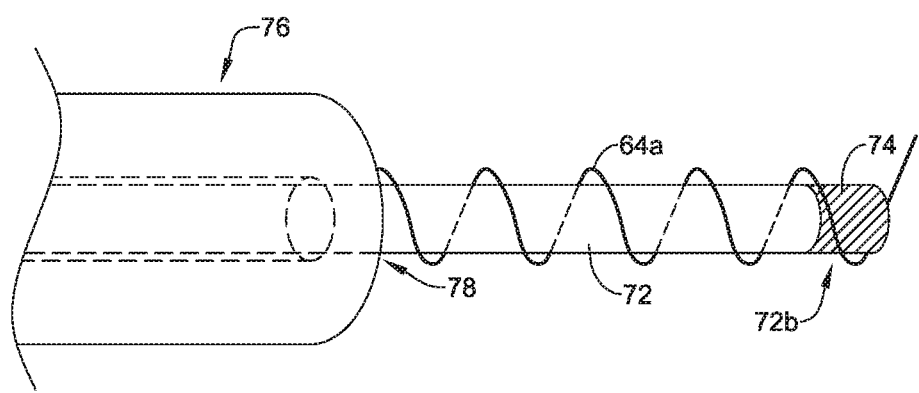
FIG. 13 is a schematic diagram showing a distal portion of an 1 MB disposed on a guide wire that has a distally-disposed guide wire electrode.

FIG. 9 is a schematic diagram of another IMD 62 that may be deployed within the heart H. The IMD 62 includes a helical screw 64 as a fixation element. In some cases, the helical screw 64 is fixed relative to the housing 50, and may be screwed into cardiac tissue by rotating the entire housing 50. In some instances, the helical screw 64 may be rotatable relative to the housing 50, and may be screwed into cardiac tissue by engaging the helical screw 64 with a tool extending through or around the housing 50. The helical screw 64 may be aligned with the longitudinal axis 54 and a wire lumen 51 may be radially offset (not shown) from the longitudinal axis 54. In some cases, the helical screw 64 may be aligned with the longitudinal axis 54 and a wire lumen 51 may extend along the longitudinal axis 54. When so provided, a guide wire passing through the wire lumen 51 may pass through the helical screw 64 as shown in FIG. 13. In some cases, the helical screw 64 may be radially offset from the longitudinal axis 54 while the wire lumen 51 may align with the longitudinal axis 54. In some instances, the helical screw 64 and the wire lumen may both be radially offset from the longitudinal axis 54.

Figure 10:
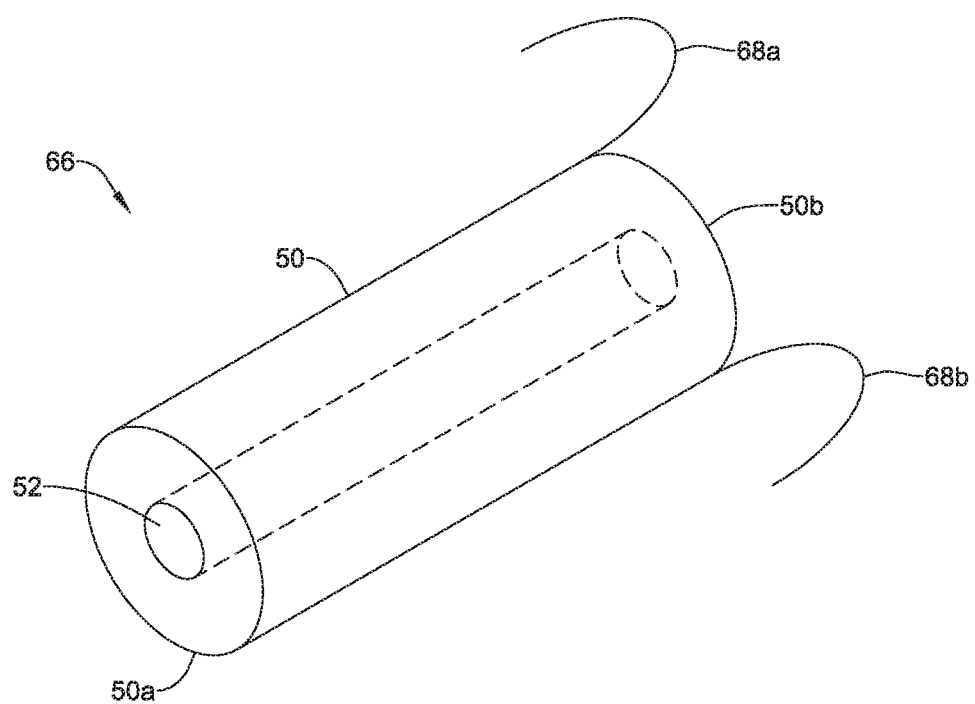
FIG. 10 is a schematic diagram of another illustrative 1 MB housing that may be delivered over a guide wire.
Figure 11:
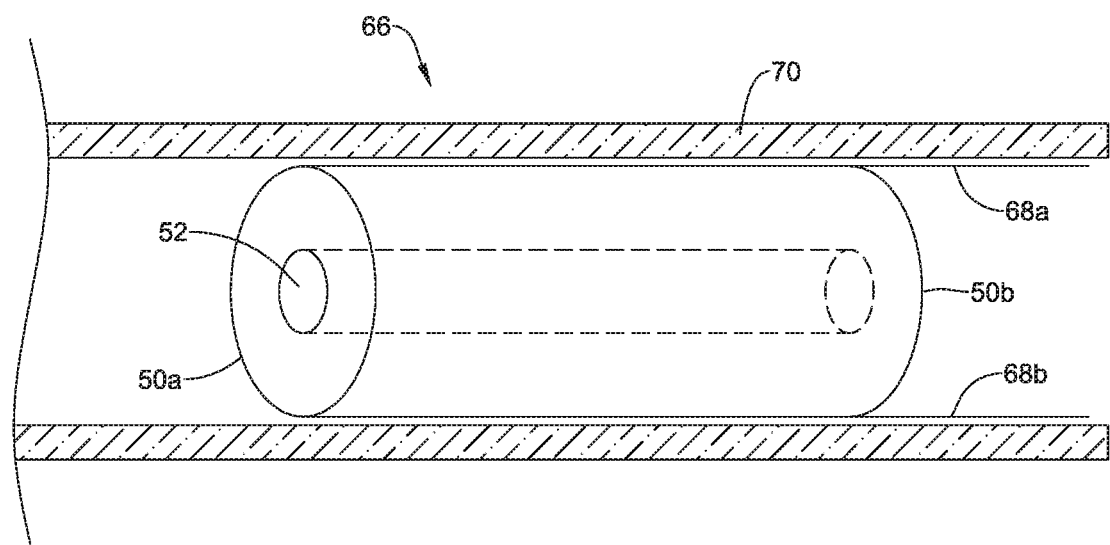
FIG. 11 is a schematic diagram of the illustrative 1 MB of FIG. 10 disposed within a delivery sheath.

FIG. 10 is a schematic diagram of another illustrative IMD 66 that may be deployed within the heart H. The IMD 66 includes tines 68*a* and 68*b* that together function as a fixation element. While two tines 68*a*, 68*b* are shown, it will be appreciated that in some cases there may be three, four or more distinct tines. FIG. 11 shows the IMD 66 disposed within a delivery sheath 70 that holds the tines 68*a*, 68*b* in a substantially linear or straight configuration that may facilitate being able to penetrate cardiac tissue. In some cases, the curved configuration of the tines 68*a*, 68*b* as shown in FIG. 10 represents a relaxed or biased configuration, and the straight configuration shown in FIG. 11 represents a temporarily altered or deformed configuration.

Figure 12:
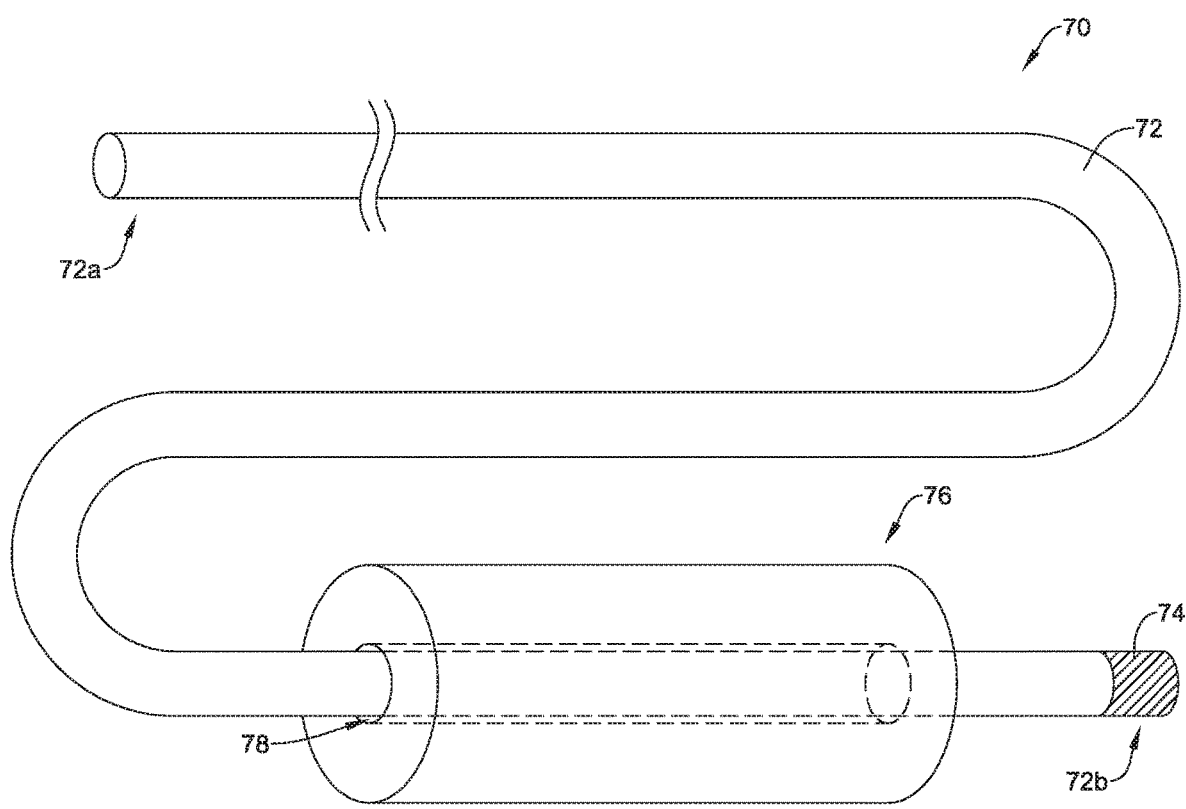
FIG. 12 is a schematic diagram of an illustrative delivery system including an IMD disposed on a guide wire that has a distally-disposed guide wire electrode.

FIG. 12 is a schematic diagram of an illustrative system 70 for delivering an IMD such as an LCP to an implantation site within the heart H. The illustrative system 70 includes an elongated guide wire 72 extending from a proximal end 72*a* to a distal end 72*b*. While not illustrated, the proximal end 72*a* may be configured with equipment that electrically couples with the guide wire 72 and/or with one or electrical conductors extending within the guide wire 72. In some cases, the guide wire 72 may include a guide wire electrode 74 that is located at or near the distal end 72*b* and that may, for example, be used to test suitability of an implantation site. The guide wire 72 may include an electrical conductor extending within the guidewire 72 and electrically coupled with the guide wire electrode 72. In some cases, the guide wire 72 may include two or more guide wire electrodes 74, each individually addressable and each being spaced at different locations along the length of the distal end of the guide wire 72. In such cases, the guide wire 72 may include several distinct electrical conductors, each electrically isolated from each other and each electrically coupled with a particular guide wire electrode. As a result, it may be possible to sequentially test an implantation site at different relative depths within the ventricular septum 10 (FIG. 1) without having to move the guide wire 72. In some cases, for example, the proximal end 72*a* of the guidewire 72 may be connected with a PSA or programmer in order to map thresholds and other electrical measurements within the ventricular septum 10 and/or on the LV facing side 14 of the ventricular septum 10 prior to delivering the IMD.

An IMD 76, that may for example represent any of the IMDs discussed here, including but not limited to the IMD 20 (FIG. 2), the IMD 34 (FIG. 3), the IMD 40 (FIG. 5), the IMD 48 (FIG. 7), the IMD 56 (FIG. 8), the IMD 62 (FIG. 9), or the IMD 66 (FIG. 10), may include a wire lumen 78 that enables the IMD 76 to be advanced over the guide wire 72. The IMD 76 may, for example, include any of the components discussed previously with respect to the other IMDs, including internal components, fixation elements, RV and LV electrodes, LV electrode supports, and the like. In some cases, for example as shown in FIG. 13, the wire lumen 78 may be aligned with a fixation helix 64*a*.

Figure 14:
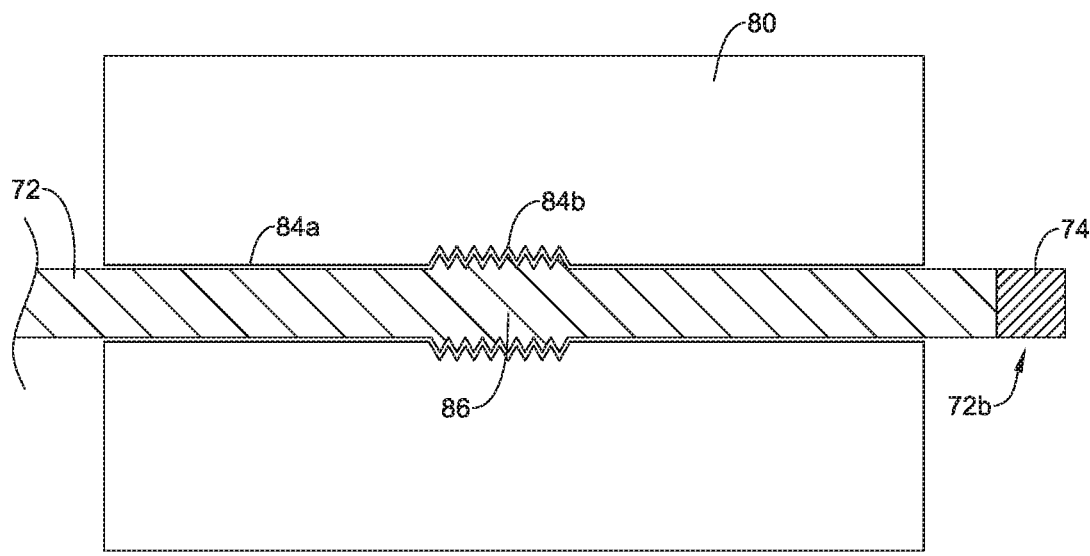
FIG. 14 is a schematic diagram showing an illustrative 1 MB disposed on a guide wire that has a distally-disposed guide wire electrode, where the guide wire provides a threaded engagement with the IMD.
Figure 15:
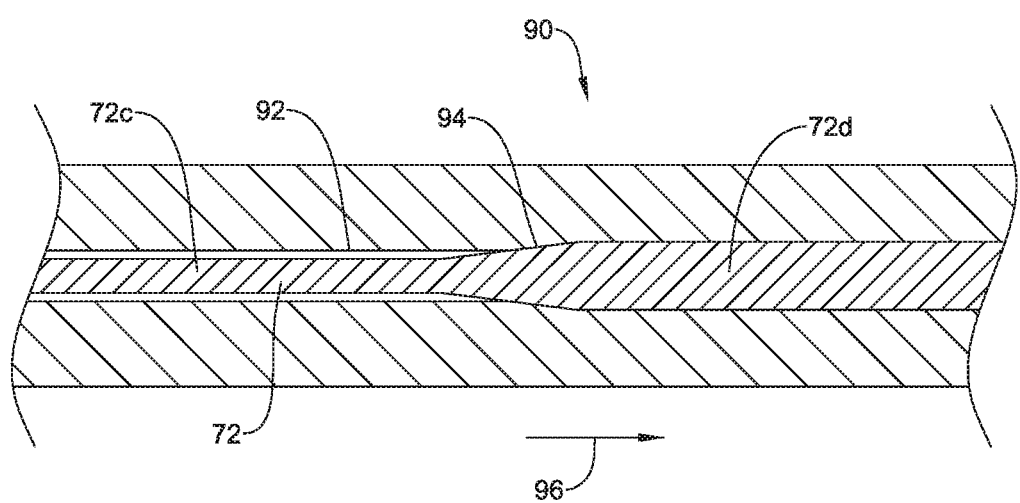
FIG. 15 is a schematic diagram showing an illustrative 1 MB disposed on a guide wire, where the guide wire provides a frictional engagement with the IMD.

In some cases, the guide wire electrode 74 on the guide wire 72, when provided, may be used not only for testing implantation sites prior to deploying the IMD 76, but may also be used as an electrode for the IMD 76 itself. In some cases, the IMD 76 may be mechanically and/or electrically coupled with the guide wire 72, and a proximal portion of the guide wire 72 may subsequently be removed. In some cases, for example, the guide wire 72 may include a narrowed or otherwise weakened portion that may be severed by applying a particular current to the guide wire 72. In some cases, a tool may be advanced over the guide wire 72 to simply cut off the proximal portion of the guide wire 72. In some cases, a distal region of the guide wire 72 may serve as a fixation element for the IMD 76, particularly if the rest of the guide wire 72 is subsequently separated and removed. FIGS. 14 and 15 provide illustrative but non-limiting ways to mechanically and/or electrically connect the IMD 76 to the guide wire 72.

In FIG. 14, an IMD 80 includes a wire lumen 84*a* defining a threaded portion 84*b*. The guide wire 72 includes a corresponding threaded portion 86 that engages the threaded portion 84*b* of the IMD 80 to provide an adjustable mechanical connection between the IMD 80 and the guide wire 72. In some cases, the threaded portion 84*b* may be electrically coupled with circuitry within the IMD 80 (such as the circuitry 26), and the threaded portion 86 may similarly be electrically coupled with an electrical connection extending through the guide wire 72 to a guide wire electrode 74. By rotating the guide wire 72 relative to the IMD 80 during implantation, the depth that the guide wire electrode 74 is placed within the septum may be controlled. It is contemplated that the IMD 80 may include a separate fixation element (not shown) to fix the IMD 80 to the septum. Alternatively, or in addition, the distal end of the guide wire 72 may be include a fixation element (e.g. helical screw) that can secure the guide wire 72 and thus the IMD 80 to the septum.

FIG. 15 shows a portion of an illustrative IMD 90 that includes a wire lumen 92 extending through the IMD 90, accommodating a guide wire 72. In some cases, the guide wire 72 may include a more proximal portion 72c having a first diameter and a more distal portion 72d having a second diameter that is greater than the first diameter. In some cases, the wire lumen 92 includes reduced diameter portion 94. In some cases, as the IMD 90 is moved distally relative to the guide wire 72, in a direction indicated by an arrow 96, the reduced diameter portion 94 will bottom out on the larger diameter more distal portion 72d of the guide wire 72. In some cases, this creates a frictional connection between the IMD 90 and the guide wire 72. In some cases, this may also provide an electrical connection between the IMD 90 and the guide wire 72.

Other structures and techniques for forming a mechanical and/or electrical connection between an IMD and the guide wire 72 are contemplated. For example, in some cases, the IMD may include a wire lumen extending therethrough that is adjustable in diameter. Once the IMD is properly positioned, the IMD may simply clamp down onto the guide wire 72, sometimes using a set screw or the like. In some cases, the IMD may include an inflatable portion that can squeeze down onto the guide wire 72. In some cases, the guide wire and the wire lumen of the IMD may provide for a bayonet style connection. These are just examples.

Figure 16:
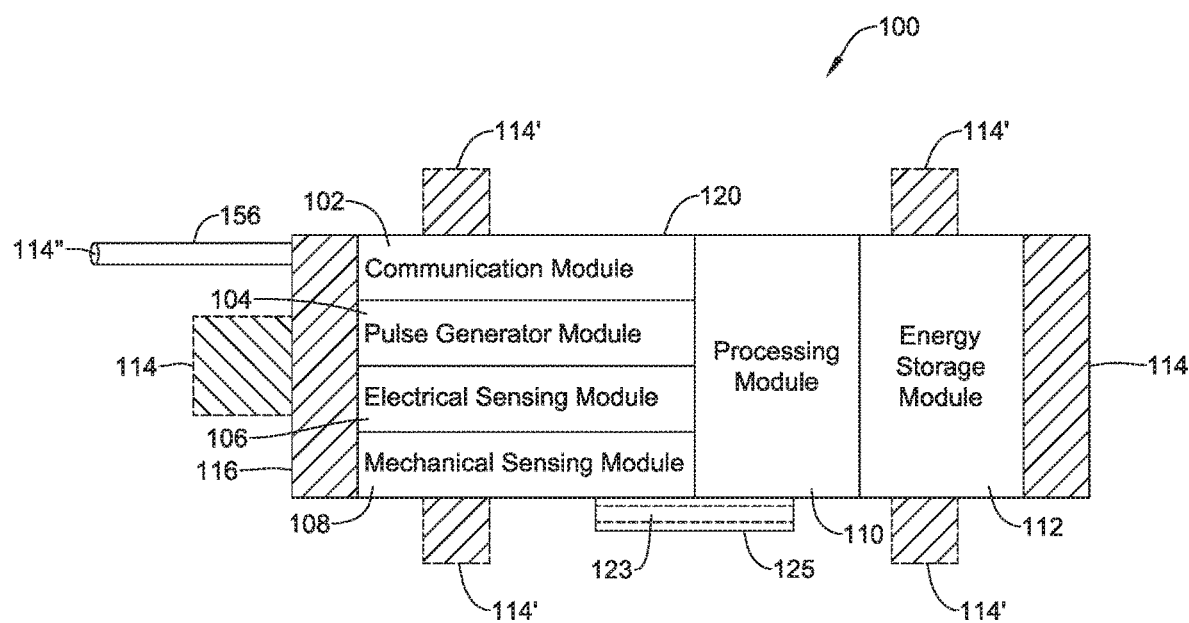
FIG. 16 is a schematic block diagram of an illustrative leadless cardiac pacemaker (LCP), which may be considered as being an example of one of the IMDs of FIGS. 2 through 15.

FIG. 16 is a conceptual schematic block diagram of an illustrative IMD, and more specifically a leadless cardiac pacemaker (LCP) that may operate to sense physiological signals and parameters and deliver one or more types of electrical stimulation therapy to the heart of the patient. Example electrical stimulation therapy may include bradycardia pacing, rate responsive pacing therapy, cardiac resynchronization therapy (CRT), anti-tachycardia pacing (ATP) therapy and/or the like. As can be seen in FIG. 16, the LCP 100 may be a compact device with all components housed within the LCP 100 or directly on a housing 120. In some instances, the LCP 100 may include one or more of a communication module 102, a pulse generator module 104, an electrical sensing module 106, a mechanical sensing module 108, a processing module 110, an energy storage module 112, and electrodes 114. The LCP 100 may, for example, be considered as being an example of the IMD 20 (FIG. 2), the IMD 34 (FIG. 3), the IMD 40 (FIG. 5), the IMD 48 (FIG. 7), the IMD 56 (FIG. 8), the IMD 62 (FIG. 9), the IMD 66 (FIG. 10), the IMD 76 (FIG. 12), the IMD 80 (FIG. 14) an/or the IMD 90 (FIG. 15).

As depicted in FIG. 16, the LCP 100 may include electrodes 114, which can be secured relative to the housing 120 and electrically exposed to tissue and/or blood surrounding the LCP 100. The electrodes 114 may generally conduct electrical signals to and from the LCP 100 and the surrounding tissue and/or blood. Such electrical signals can include communication signals, electrical stimulation pulses, and intrinsic cardiac electrical signals, to name a few. Intrinsic cardiac electrical signals may include electrical signals generated by the heart and may be represented by an electrocardiogram (ECG).

The electrodes 114 may include one or more biocompatible conductive materials such as various metals or alloys that are known to be safe for implantation within a human body. In some instances, the electrodes 114 may be generally disposed on either end of the LCP 100 and may be in electrical communication with one or more of modules the 102, 104, 106, 108, and 110. In embodiments where the electrodes 114 are secured directly to the housing 120, an insulative material may electrically isolate the electrodes 114 from adjacent electrodes, the housing 120, and/or other parts of the LCP 100. In some instances, some or all of the electrodes 114 may be spaced from the housing 120 and may be connected to the housing 120 and/or other components of the LCP 100 through connecting wires. In such instances, the electrodes 114 may be placed on a tail (not shown) that extends out away from the housing 120. As shown in FIG. 16, in some embodiments, the LCP 100 may include electrodes 114'. The electrodes 114' may be in addition to the electrodes 114, or may replace one or more of the electrodes 114. The electrodes 114' may be similar to the electrodes 114 except that the electrodes 114' are disposed on the sides of the LCP 100. In some cases, the electrodes 114' may increase the number of electrodes by which the LCP 100 may deliver communication signals and/or electrical stimulation pulses, and/or may sense intrinsic cardiac electrical signals, communication signals, and/or electrical stimulation pulses.

The electrodes 114 and/or 114' may assume any of a variety of sizes and/or shapes, and may be spaced at any of a variety of spacings. For example, the electrodes 114 may have an outer diameter of two to twenty millimeters (mm). In other embodiments, the electrodes 114 and/or 114' may have a diameter of two, three, five, seven millimeters (mm), or any other suitable diameter, dimension and/or shape. Example lengths for the electrodes 114 and/or 114' may include, for example, one, three, five, ten millimeters (mm), or any other suitable length. As used herein, the length is a dimension of the electrodes 114 and/or 114' that extends away from the outer surface of the housing 120. In some instances, at least some of the electrodes 114 and/or 114' may be spaced from one another by a distance of twenty, thirty, forty, fifty millimeters (mm), or any other suitable spacing. The electrodes 114 and/or 114' of a single device may have different sizes with respect to each other, and the spacing and/or lengths of the electrodes on the device may or may not be uniform.

In some instances, an LV electrode 114" may also be provided. The LV electrode 114" may be supported by an LV electrode support 156 that extends away from the housing 120. In some cases, the LV electrode support 156 is configured to place the LV electrode 114" within the ventricular septum 10, and in electrical communication with conduction pathways extending through the ventricular septum 10 that control the contraction of the LV. In some instances, the LV electrode support 156 may extend entirely through the ventricular septum 10 in order to place an LV electrode 114" within the LV and in contact with the LV facing side 14 of the ventricular septum 10.

In some cases, a wire lumen 123 may be provided. The wire lumen 123 may take a variety of forms. For example, the wire lumen 123 may extend through the housing of the LCP 100 from the first end to the second end. In some cases, as discussed herein, the wire lumen 123 may be concentric with the housing of the LCP 100, and the wire lumen 123 may traverse along a longitudinal axis of the housing of the LCP 100. In other cases, the wire lumen 123 may be parallel with the longitudinal axis of the LCP 100 but radially offset from the longitudinal axis. In some cases, as shown in FIG. 16 for example, an LCP 100 may include a tubular structure 125 that is secured to an outer surface of the housing of the LCP 100. The tubular structure 125 may define the wire lumen 123 for receiving a guide wire.

In the embodiment shown, the communication module 102 may be electrically coupled to two or more of the electrodes 114, 114' and/or 114" and may be configured to deliver communication pulses to tissues of the patient for communicating with other devices such as sensors, programmers, other medical devices, and/or the like. Communication signals, as used herein, may be any modulated signal that conveys information to another device, either by itself or in conjunction with one or more other modulated signals. In some embodiments, communication signals may be limited to sub-threshold signals that do not result in capture of the heart yet still convey information. The communication signals may be delivered to another device that is located either external or internal to the patient's body. In some instances, the communication may take the form of distinct communication pulses separated by various amounts of time. In some of these cases, the timing between successive pulses may convey information. The communication module 102 may additionally be configured to sense for communication signals delivered by other devices, which may be located external or internal to the patient's body.

The communication module 102 may communicate to help accomplish one or more desired functions. Some example functions include delivering sensed data, using communicated data for determining occurrences of events such as arrhythmias, coordinating delivery of electrical stimulation therapy, and/or other functions. In some cases, the LCP 100 may use communication signals to communicate raw information, processed information, messages and/or commands, and/or other data. Raw information may include information such as sensed electrical signals (e.g. a sensed ECG), signals gathered from coupled sensors, and the like. In some embodiments, the processed information may include signals that have been filtered using one or more signal processing techniques. Processed information may also include parameters and/or events that are determined by the LCP 100 and/or another device, such as a determined heart rate, timing of determined heartbeats, timing of other determined events, determinations of threshold crossings, expirations of monitored time periods, accelerometer signals, activity level parameters, blood-oxygen parameters, blood pressure parameters, heart sound parameters, and the like. In some cases, processed information may, for example, be provided by a chemical sensor or an optically interfaced sensor. Messages and/or commands may include instructions or the like directing another device to take action, notifications of imminent actions of the sending device, requests for reading from the receiving device, requests for writing data to the receiving device, information messages, and/or other messages commands.

In at least some embodiments, the communication module 102 (or the LCP 100) may further include switching circuitry to selectively connect one or more of the electrodes 114, 114' and/or 114" to the communication module 102 in order to select which of the electrodes 114, 114' and/or 114" that the communication module 102 delivers communication pulses with. It is contemplated that the communication module 102 may be communicating with other devices via conducted signals, radio frequency (RF) signals, optical signals, acoustic signals, inductive coupling, and/or any other suitable communication methodology. Where the communication module 102 generates electrical communication signals, the communication module 102 may include one or more capacitor elements and/or other charge storage devices to aid in generating and delivering communication signals. In the embodiment shown, the communication module 102 may use energy stored in the energy storage module 112 to generate the communication signals. In at least some examples, the communication module 102 may include a switching circuit that is connected to the energy storage module 112 and, with the switching circuitry, may connect the energy storage module 112 to one or more of the electrodes 114/114'/114" to generate the communication signals.

As shown in FIG. 16, a pulse generator module 104 may be electrically connected to one or more of the electrodes 114, 114' and/or 114". The pulse generator module 104 may be configured to generate electrical stimulation pulses and deliver the electrical stimulation pulses to tissues of a patient via one or more of the electrodes 114, 114' and/or 114" in order to effectuate one or more electrical stimulation therapies. Electrical stimulation pulses as used herein are meant to encompass any electrical signals that may be delivered to tissue of a patient for purposes of treatment of any type of disease or abnormality. For example, when used to treat heart disease, the pulse generator module 104 may generate electrical stimulation pacing pulses for capturing the heart of the patient, i.e. causing the heart to contract in response to the delivered electrical stimulation pulse. In some of these cases, the LCP 100 may vary the rate at which the pulse generator module 104 generates the electrical stimulation pulses, for example in rate adaptive pacing. In other embodiments, the electrical stimulation pulses may include defibrillation/cardioversion pulses for shocking the heart out of fibrillation or into a normal heart rhythm. In yet other embodiments, the electrical stimulation pulses may include anti-tachycardia pacing (ATP) pulses. It should be understood that these are just some examples. The pulse generator module 104 may include one or more capacitor elements and/or other charge storage devices to aid in generating and delivering appropriate electrical stimulation pulses. In at least some embodiments, the pulse generator module 104 may use energy stored in the energy storage module 112 to generate the electrical stimulation pulses. In some particular embodiments, the pulse generator module 104 may include a switching circuit that is connected to the energy storage module 112 and may connect the energy storage module 112 to one or more of the electrodes 114/114'/114" to generate electrical stimulation pulses. In some cases, the pulse generator module 104 may provide pacing pulses to pace the RV of the heart H using electrode 114, and may provide pacing pulses to the LV of the heart H using electrode 114". In some cases, the pacing pulses generated for pacing the RV of the heart H by the pulse generator module 104 may be offset in time, have a different duration, have a different amplitude and/or have a different shape from the pacing pulses generated by the pulse generator module 104 for pacing the LV of the heart H, if desired.

The LCP 100 may further include an electrical sensing module 106 and a mechanical sensing module 108. The electrical sensing module 106 may be configured to sense intrinsic cardiac electrical signals conducted from the electrodes 114, 114' and/or 114" to the electrical sensing module 106. For example, the electrical sensing module 106 may be electrically connected to one or more of the electrodes 114, 114' and/or 114" and the electrical sensing module 106 may be configured to receive cardiac electrical signals conducted through the electrodes 114, 114' and/or 114" via a sensor amplifier or the like. In some embodiments, the cardiac electrical signals from electrodes 114 and/or 114' may represent local information from the RV, while the cardiac electrical signals from LV electrode 114" may represent local information from the LV of the heart H.

The mechanical sensing module 108 may include, or be electrically connected to, various sensors, such as accelerometers, including multi-axis accelerometers such as two- or three-axis accelerometers, gyroscopes, including multi-axis gyroscopes such as two- or three-axis gyroscopes, blood pressure sensors, heart sound sensors, piezoelectric sensors, blood-oxygen sensors, and/or other sensors which measure one or more physiological parameters of the heart and/or patient. Mechanical sensing module 108, when present, may gather signals from the sensors indicative of the various physiological parameters. The electrical sensing module 106 and the mechanical sensing module 108 may both be connected to the processing module 110 and may provide signals representative of the sensed cardiac electrical signals and/or physiological signals to the processing module 110. Although described with respect to FIG. 16 as separate sensing modules, in some embodiments, the electrical sensing module 106 and the mechanical sensing module 108 may be combined into a single module. In at least some examples, the LCP 100 may only include one of the electrical sensing module 106 and the mechanical sensing module 108. In some cases, any combination of the processing module 110, the electrical sensing module 106, the mechanical sensing module 108, the communication module 102, the pulse generator module 104 and/or the energy storage module may be considered a controller of the LCP 100.

The processing module 110 may be configured to direct the operation of the LCP 100 and may, in some embodiments, be termed a controller. For example, the processing module 110 may be configured to receive cardiac electrical signals from the electrical sensing module 106 and/or physiological signals from the mechanical sensing module 108. Based on the received signals, the processing module 110 may determine, for example, occurrences and types of arrhythmias and other determinations such as whether the LCP 100 has become dislodged. The processing module 110 may further receive information from the communication module 102. In some embodiments, the processing module 110 may additionally use such received information to determine occurrences and types of arrhythmias and/or and other determinations such as whether the LCP 100 has become dislodged. In still some additional embodiments, the LCP 100 may use the received information instead of the signals received from the electrical sensing module 106 and/or the mechanical sensing module 108—for instance if the received information is deemed to be more accurate than the signals received from the electrical sensing module 106 and/or the mechanical sensing module 108 or if the electrical sensing module 106 and/or the mechanical sensing module 108 have been disabled or omitted from the LCP 100.

After determining an occurrence of an arrhythmia, the processing module 110 may control the pulse generator module 104 to generate electrical stimulation pulses in accordance with one or more electrical stimulation therapies to treat the determined arrhythmia. For example, the processing module 110 may control the pulse generator module 104 to generate pacing pulses with varying parameters and in different sequences to effectuate one or more electrical stimulation therapies. As one example, in controlling the pulse generator module 104 to deliver bradycardia pacing therapy, the processing module 110 may control the pulse generator module 104 to deliver pacing pulses designed to capture the heart of the patient at a regular interval to help prevent the heart of a patient from falling below a predetermined threshold. In some cases, the rate of pacing may be increased with an increased activity level of the patient (e.g. rate adaptive pacing). For instance, the processing module 110 may monitor one or more physiological parameters of the patient which may indicate a need for an increased heart rate (e.g. due to increased metabolic demand). The processing module 110 may then increase the rate at which the pulse generator module 104 generates electrical stimulation pulses. Adjusting the rate of delivery of the electrical stimulation pulses based on the one or more physiological parameters may extend the battery life of the LCP 100 by only requiring higher rates of delivery of electrical stimulation pulses when the physiological parameters indicate there is a need for increased cardiac output. Additionally, adjusting the rate of delivery of the electrical stimulation pulses may increase a comfort level of the patient by more closely matching the rate of delivery of electrical stimulation pulses with the cardiac output need of the patient.

For ATP therapy, the processing module 110 may control the pulse generator module 104 to deliver pacing pulses at a rate faster than an intrinsic heart rate of a patient in attempt to force the heart to beat in response to the delivered pacing pulses rather than in response to intrinsic cardiac electrical signals. Once the heart is following the pacing pulses, the processing module 110 may control the pulse generator module 104 to reduce the rate of delivered pacing pulses down to a safer level. In CRT, the processing module 110 may control the pulse generator module 104 to deliver pacing pulses in coordination with another device to cause the heart to contract more efficiently. In cases where the pulse generator module 104 is capable of generating defibrillation and/or cardioversion pulses for defibrillation/cardioversion therapy, the processing module 110 may control the pulse generator module 104 to generate such defibrillation and/or cardioversion pulses. In some cases, the processing module 110 may control the pulse generator module 104 to generate electrical stimulation pulses to provide electrical stimulation therapies different than those examples described above.

Aside from controlling the pulse generator module 104 to generate different types of electrical stimulation pulses and in different sequences, in some embodiments, the processing module 110 may also control the pulse generator module 104 to generate the various electrical stimulation pulses with varying pulse parameters. For example, each electrical stimulation pulse may have a pulse width and a pulse amplitude. The processing module 110 may control the pulse generator module 104 to generate the various electrical stimulation pulses with specific pulse widths and pulse amplitudes. For example, the processing module 110 may cause the pulse generator module 104 to adjust the pulse width and/or the pulse amplitude of electrical stimulation pulses if the electrical stimulation pulses are not effectively capturing the heart (e.g. RV or LV capture). Such control of the specific parameters of the various electrical stimulation pulses may help the LCP 100 provide more effective delivery of electrical stimulation therapy.

In some embodiments, the processing module 110 may further control the communication module 102 to send information to other devices. For example, the processing module 110 may control the communication module 102 to generate one or more communication signals for communicating with other devices of a system of devices. For instance, the processing module 110 may control the communication module 102 to generate communication signals in particular pulse sequences, where the specific sequences convey different information. The communication module 102 may also receive communication signals for potential action by the processing module 110.

In further embodiments, the processing module 110 may control switching circuitry by which the communication module 102 and the pulse generator module 104 deliver communication signals and/or electrical stimulation pulses to tissue of the patient. As described above, both the communication module 102 and the pulse generator module 104 may include circuitry for connecting one or more of the electrodes 114, 114' and/or 114" to the communication module 102 and/or the pulse generator module 104 so those modules may deliver the communication signals and electrical stimulation pulses to tissue of the patient. The specific combination of one or more electrodes by which the communication module 102 and/or the pulse generator module 104 deliver communication signals and electrical stimulation pulses may influence the reception of communication signals and/or the effectiveness of electrical stimulation pulses. Although it was described that each of the communication module 102 and the pulse generator module 104 may include switching circuitry, in some embodiments, the LCP 100 may have a single switching module connected to the communication module 102, the pulse generator module 104, and the electrodes 114, 114' and/or 114". In such embodiments, processing module 110 may control the switching module to connect the modules 102/104 and the electrodes 114/114'/114" as appropriate. In some cases, the LV electrode 114" may also be coupled to the switching module and may be used for communication.

In some embodiments, the processing module 110 may include a pre-programmed chip, such as a very-large-scale integration (VLSI) chip or an application specific integrated circuit (ASIC). In such embodiments, the chip may be pre-programmed with control logic in order to control the operation of the LCP 100. By using a pre-programmed chip, the processing module 110 may use less power than other programmable circuits while able to maintain basic functionality, thereby potentially increasing the battery life of the LCP 100. In other instances, the processing module 110 may include a programmable microprocessor or the like. Such a programmable microprocessor may allow a user to adjust the control logic of the LCP 100 after manufacture, thereby allowing for greater flexibility of the LCP 100 than when using a pre-programmed chip. In still other embodiments, the processing module 110 may not be a single component. For example, the processing module 110 may include multiple components positioned at disparate locations within the LCP 100 in order to perform the various described functions. For example, certain functions may be performed in one component of the processing module 110, while other functions are performed in a separate component of the processing module 110.

The processing module 110, in additional embodiments, may include a memory circuit and the processing module 110 may store information on and read information from the memory circuit. In other embodiments, the LCP 100 may include a separate memory circuit (not shown) that is in communication with the processing module 110, such that the processing module 110 may read and write information to and from the separate memory circuit. The memory circuit, whether part of the processing module 110 or separate from the processing module 110, may be volatile memory, non-volatile memory, or a combination of volatile memory and non-volatile memory.

The energy storage module 112 may provide a power source to the LCP 100 for its operations. In some embodiments, the energy storage module 112 may be a non-rechargeable lithium-based battery. In other embodiments, the non-rechargeable battery may be made from other suitable materials. In some embodiments, the energy storage module 112 may be considered to be a rechargeable power supply, such as but not limited to, a rechargeable battery. In still other embodiments, the energy storage module 112 may include other types of energy storage devices such as capacitors or super capacitors. In some cases, as will be discussed, the energy storage module 112 may include a rechargeable primary battery and a non-rechargeable secondary battery. In some cases, the primary battery and the second battery, if present, may both be rechargeable.

In some cases, to implant the LCP 100 inside a patient's body, an operator (e.g., a physician, clinician, etc.) may move the LCP 100 to a desired implantation site and fix the LCP 100 to the cardiac tissue of the patient's heart. To facilitate fixation, the LCP 100 may include one or more anchors schematically shown at 116. The one or more anchors 116 may include any number of fixation or anchoring mechanisms. For example, one or more anchors 116 may include one or more pins, staples, threads, screws, helix, tines, and/or the like. In some embodiments, although not shown, one or more anchors 116 may include threads on its external surface that may run along at least a partial length of an anchor member. The threads may provide friction between the cardiac tissue and the anchor to help fix the anchor member within the cardiac tissue. In some cases, the one or more anchors 116 may include an anchor member that has a cork-screw shape that can be screwed into the cardiac tissue. In other embodiments, the anchor 116 may include other structures such as barbs, spikes, or the like to facilitate engagement with the surrounding cardiac tissue. In some cases, the LV electrode support 156 may anchor the LCP 100.

Figure 17:
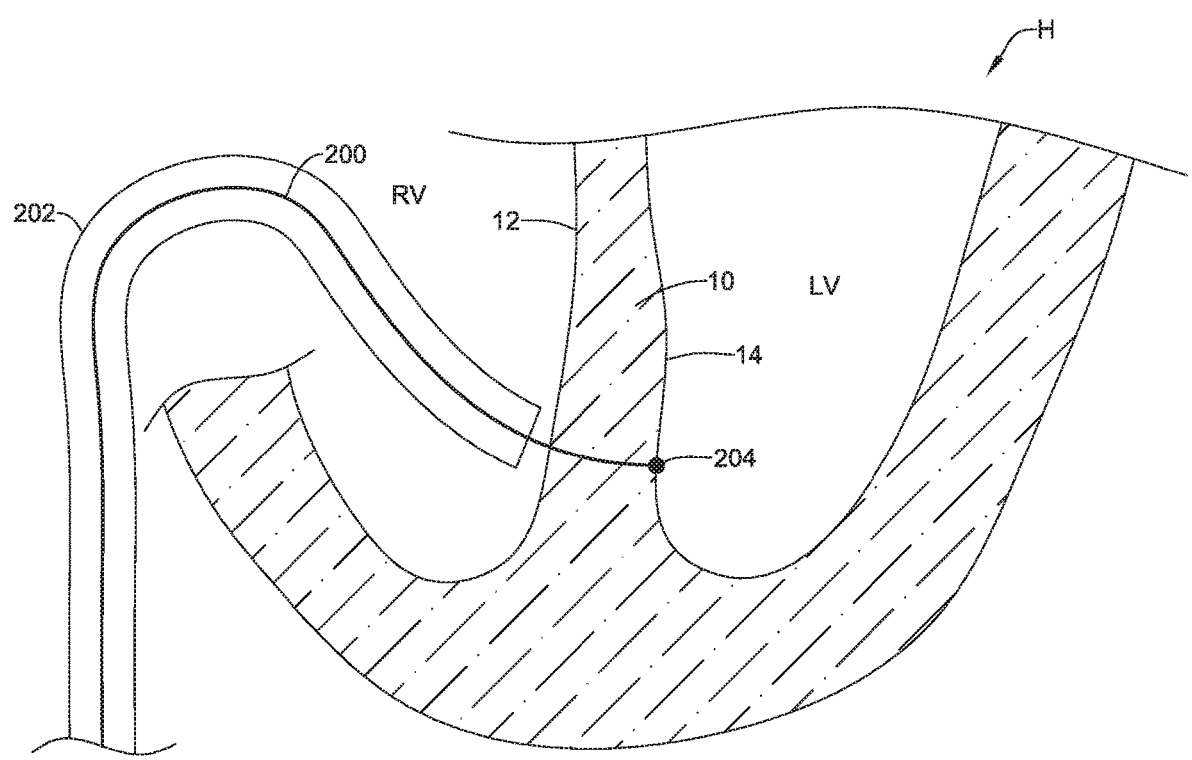
FIGS. 17 through 21 show an illustrative but non-limiting example of delivering and deploying an LCP over a guide wire.
Figure 18:
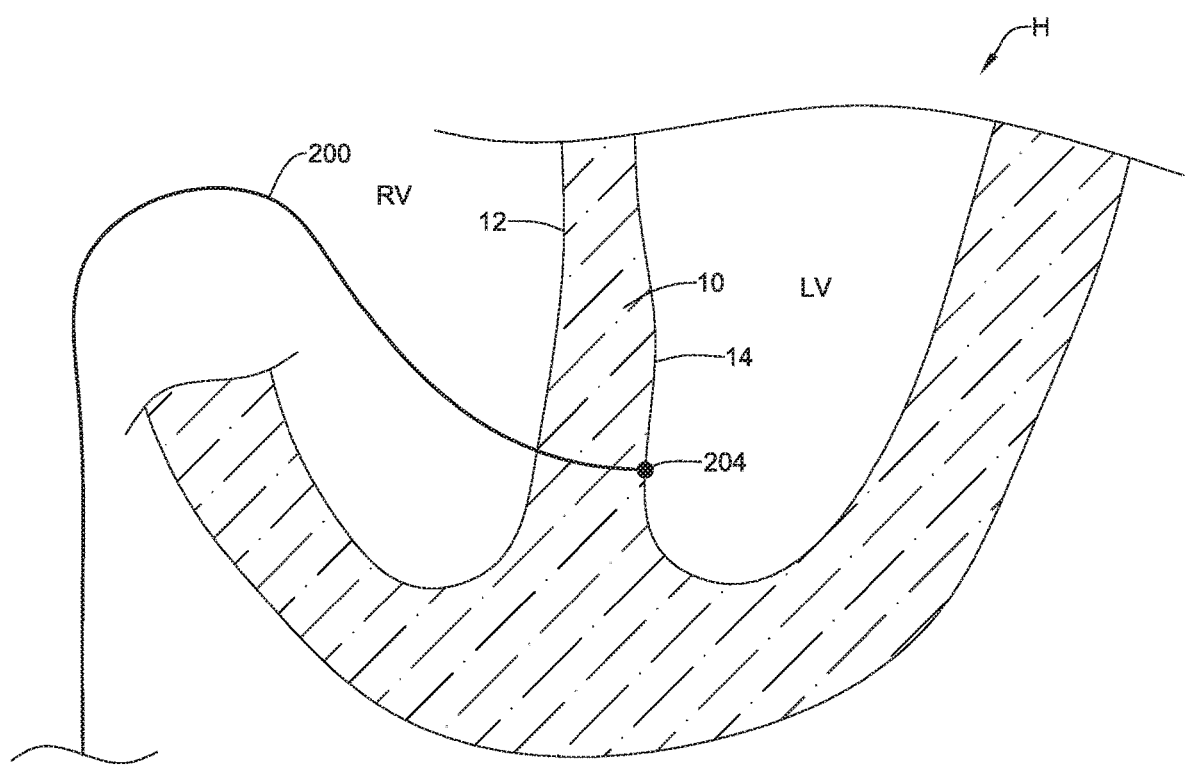

FIGS. 17 through 21 provide an illustrative but non-limiting example of a procedure for implanting an IMD within the heart. While the illustrated procedure shows implantation of an LCP within the right ventricle RV, it will be appreciated that this procedure could be used to place an LCP elsewhere within the heart. As shown in FIG. 17, a guide wire 200 has been advanced within a catheter 202 that has reached a position within the right ventricle RV, proximate the RV facing side 12 of the ventricular septum 10. In the example shown, the guide wire 200 has been advanced into and through the ventricular septum 10 such that a guide wire electrode 204 at a distal end of the guide wire 200 is within the left ventricle LV proximate the LV facing side 14 of the ventricular septum 10. In some cases, it is contemplated that the guide wire electrode 204 may instead only penetrate part way through the ventricular septum 10 and still be effective at pacing the LV. In some cases, the guide wire 200 may include a fixation element to at least temporarily secure the guide wire 200 in this position, but this is not required. Once the guide wire 200 is in position, the catheter 202 may be withdrawn, as shown for example in FIG. 18.

Figure 19:
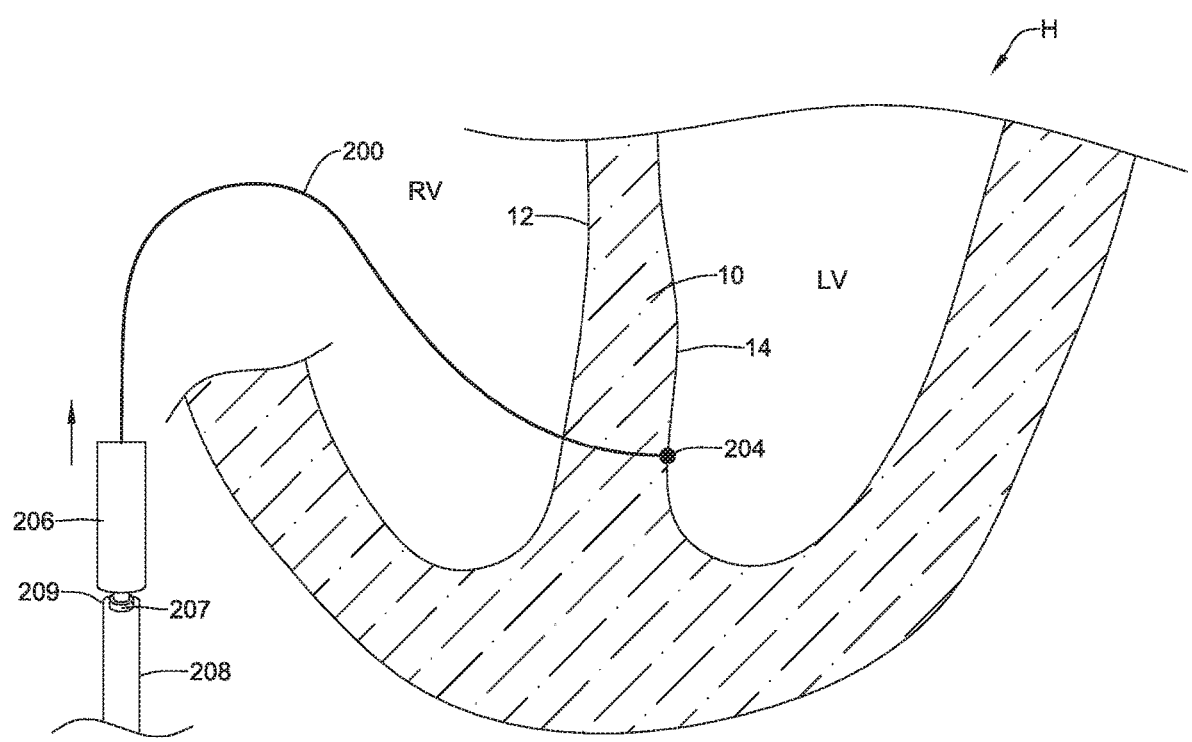
Figure 20:
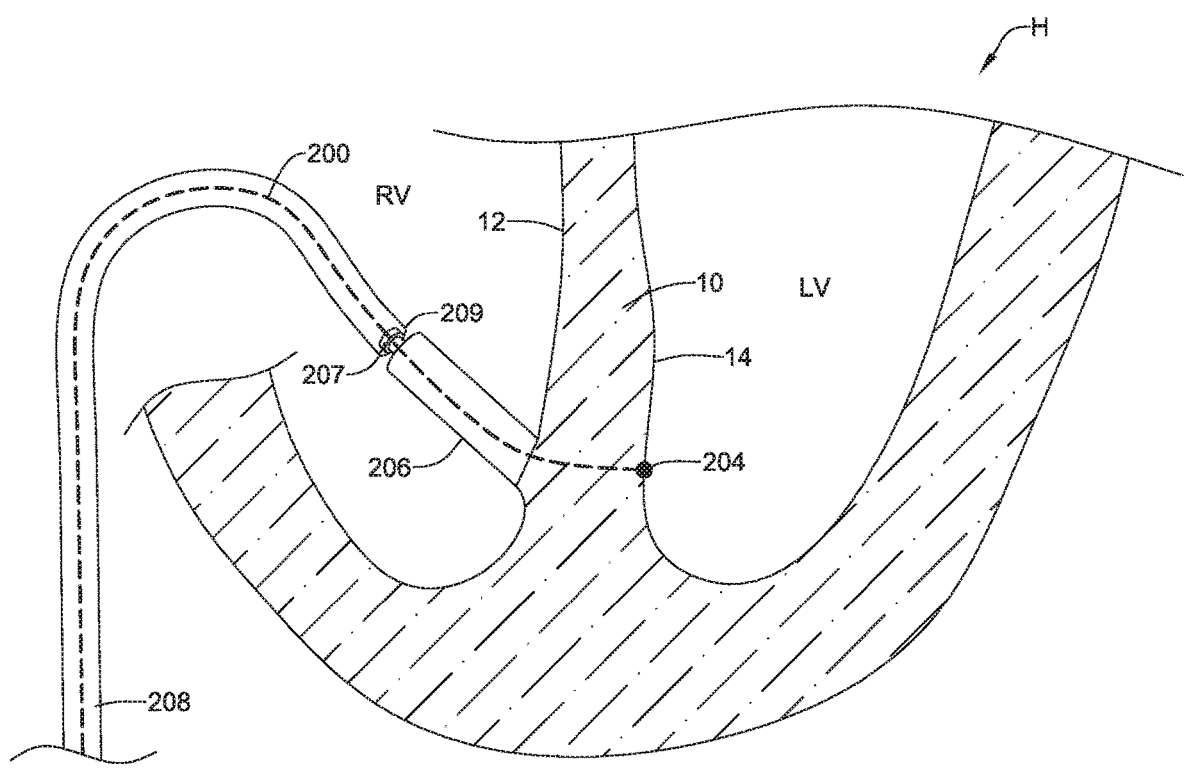

Moving to FIG. 19, an LCP 206 is being advanced over the guide wire 200 with the assistance of an LCP pusher 208. The LCP pusher 208 may in some cases include a sheath that extends around and houses the LCP during delivery, but this is not required or even desired in all embodiments. In some cases, the LCP 206 may include a feature 207 that enables a corresponding grasping feature 209 on the LCP pusher 208 to hold onto the LCP 206 while the LCP 206 and the LCP pusher 208 are advanced over the guide wire 200. In any event, the LCP 206 is advanced over the guide wire 200 until the LCP 206 reaches a position proximate the RV facing side 12 of the ventricular septum 10, as shown in FIG. 20. It will be appreciated that in some cases, a guide wire lumen extending through the LCP 206 may extend concentrically through the feature 207. In some instances, the guide wire lumen extending through the LCP 206, to accommodate the guide wire 200, may be radially offset from the feature 207.

Figure 21:
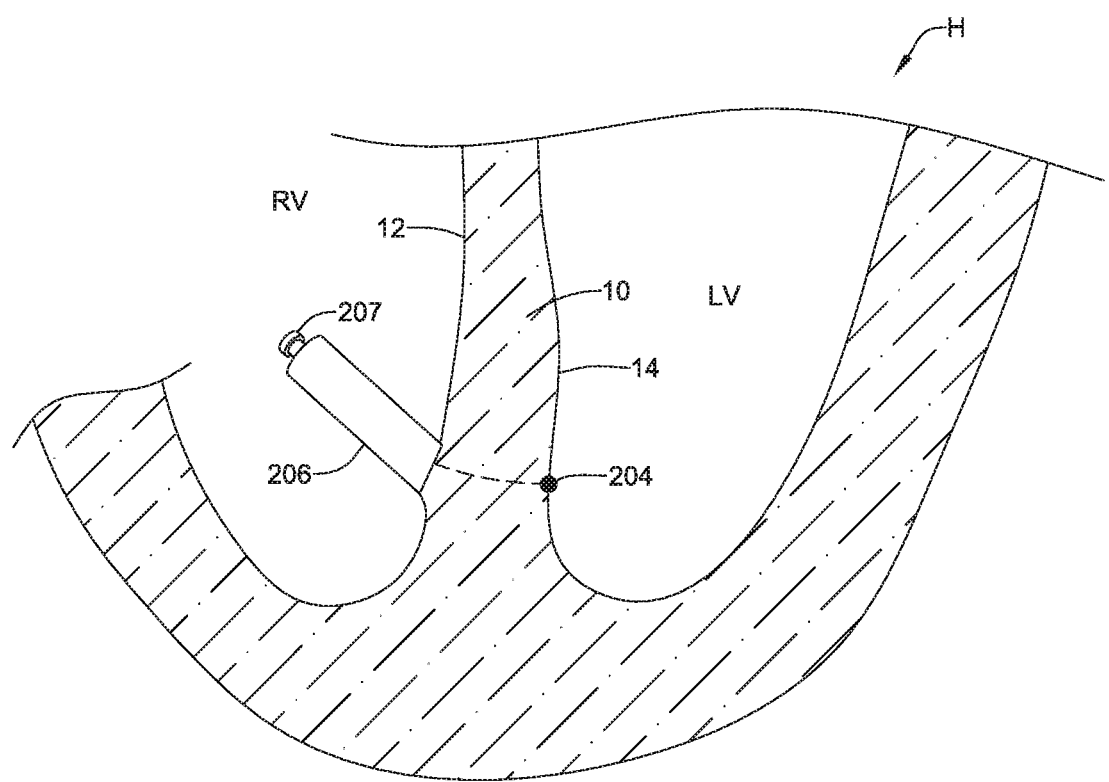

At this point, a fixation element such as the fixation element 32 (FIG. 3) or the fixation element 42 (FIG. 5) may be advanced into the ventricular septum 10. In some cases, the distal end of the guidewire 200, including the guide wire electrode 204, may serve as an anchoring mechanism for the LCP 206. In some cases, the distal end of the guide wire 200 may include a hook or other shape to facilitate fixation. In some instances, the guide wire electrode 204 may serve as an LV electrode for the LCP 206. In some cases, an LV electrode support such as the LV electrode support 36 (FIG. 3) may be advanced into the ventricular septum 10. In some cases, the LCP pusher 208 may be used to advance a fixation element and/or an LV electrode support. In some cases, the LCP pusher 208 may be used to actuate a fixation helix. In some cases, particularly of the distal end of the guide wire 200 is to be used as a fixation element for the LCP 206, and/or if the distal end of the guide wire 200, including the guide wire electrode 204, is to be used as an LV electrode for the LCP 200, a tool may be advanced over the guide wire 204 in order to snip off a proximal portion of the guide wire 200, leaving a distal portion of the guide wire 200, including the guide wire electrode 204, in place. FIG. 21 illustrates the LCP 206 after implantation.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments.

What is claimed is:

1. A leadless cardiac pacemaker (LCP) system for pacing a patient's heart from within a right ventricle of a patient's heart, the patient's heart including a ventricular septum dividing the right ventricle from a left ventricle, the LCP configured for delivery to an implantation site on the right ventricle side of the ventricle septum, the LCP system comprising:
   a guide wire including a guide wire electrode, the guide wire configured to be deployed within the right ventricle and penetrating the ventricle septum sufficiently far to allow the guide wire electrode to capture conduction pathways of the left ventricle;
   a housing configured to be positioned within the right ventricle of the patient's heart proximate the ventricular septum once the LCP is implanted at the implantation site on a right ventricle side of the ventricle septum, the housing configured to be advanced over the guide wire during implantation;
   a power source disposed within the housing;
   circuitry disposed within the housing and operatively coupled to the power source;
   a right ventricle (RV) electrode fixed to the housing and positioned to contact the right ventricular side of the ventricular septum once the LCP is implanted at the implantation site on the right ventricle side of the ventricle septum, the circuitry is configured to pace the patient's right ventricle via the RV electrode;
   the guide wire electrode operably coupled to the circuitry, the circuitry further configured to pace the patient's left ventricle via the guide wire electrode;
   wherein a proximal portion of the guide wire is removed after the housing is advanced over the guide wire during implantation of the LCP.

2. The LCP system of claim 1, further comprising a fixation element for extending into the ventricular septum at the implantation site on the right ventricle side of the ventricle septum to fix the LCP relative to the ventricular septum at the implantation site, wherein the fixation element is fixed to the housing of the LCP and delivered along with the LCP to the implantation site; and
   wherein the fixation element is configured to engage the ventricular septum once the LCP is at the implantation site on the right ventricle side of the ventricle septum and to fix the LCP relative to the ventricular septum with the RV electrode of the LCP positioned to allow the RV electrode to capture conduction pathways of the right ventricle within the ventricular septum.

3. The LCP system of claim 2, wherein the fixation element comprises a helical screw.

4. The LCP system of claim 3, wherein the helical screw is secured relative to the housing via threads, and the helical screw is advanced distally relative to the housing by rotating the helical screw relative to the housing.

5. The LCP system of claim 4, wherein the helical screw is rotated relative to the housing by an LCP pusher that is configured to push the LCP along the guide wire to the implantation site and also rotate the helical screw relative to the housing.

6. The LCP system of claim 2, wherein the fixation element comprises one or more tines.

7. The LCP system of claim 6, wherein the one or more tines are configured to extend distally of the housing and bend outward, and wherein the one or more tines are confined by a LCP delivery sheath that extends over the LCP and the one or more tines while the LCP is delivered over the guide wire to the implantation site.

8. The LCP system of claim 7, wherein the one or more tines are configured to extend into the ventricular septum and bend outward when the LCP is pushed out of the LCP delivery sheath at the implantation site.

9. The LCP system of claim 1, further comprising a wire lumen configured to permit the LCP to slide over the guide wire to the implantation site, wherein the wire lumen is offset from a central axis of the housing.

10. The LCP system of claim 1, further comprising a left ventricle electrode support extending distally away from the housing and configured to penetrate the septum of the patient's heart; and
    the left ventricle electrode support includes one or more LV electrodes supported by the LV electrode support each spaced at a different distance distally from the housing, the two or more LV electrodes operatively coupled with the circuitry that is disposed within the housing with each independently selectable by the circuitry.

11. The LCP system of claim 10, further comprising:
    one or more additional left ventricle (LV) electrodes supported by a fixation element each spaced at a different distance distally from the housing, the one or more additional LV electrodes operatively coupled with the circuitry that is disposed within the housing with each independently selectable by the circuitry.

12. A system for delivering a leadless cardiac pacemaker (LCP) to an implantation site within a right ventricle of a patient's heart, the patient's heart including a ventricular septum dividing the right ventricle from a left ventricle, the system comprising:

an elongated guide wire configured to extend transvascularly to within the chamber of the patient's heart and to the implantation site on the right ventricle side of the ventricle septum, the elongated guide wire including a guide wire electrode at or near its distal end that is usable to test suitability of the implantation site and to serve as a left ventricle (LV) electrode after implantation; and an LCP comprising:
- a housing configured to be positioned within the right ventricle of the patient's heart proximate the right ventricle side of the ventricular septum once implanted at the implantation site;
- a power source disposed within the housing;
- circuitry disposed within the housing and operably coupled to the power source;
- two or more electrodes disposed relative to the housing including one or more right ventricle (RV) electrodes positioned to contact the right ventricle side of the ventricular septum once the LCP has been implanted at the implantation site, and the LV electrode configured to sufficiently penetrate the ventricular septum to allow the LV electrode to capture conduction pathways of the left ventricle within the ventricular septum;
- wherein the circuitry is configured to pace the right ventricle via the one or more RV electrodes and the left ventricle via the LV electrode;
- a wire lumen configured to permit the LCP to slide over the elongated guide wire to the implantation site; and
- a fixation element for extending into the chamber wall at the implantation site to fix the LCP relative to the ventricular septum at the implantation site, wherein the fixation element is fixed to the LCP and delivered along with the LCP to the implantation site.

13. The system of claim 12, wherein the wire lumen extends through the LCP along a longitudinal axis of the LCP.

14. The system of claim 12, wherein the elongated guide wire is configured to pierce at least partially through the ventricular septum at the implantation site with the entire guide wire electrode positioned inside of the ventricular septum.

15. The system of claim 12, wherein the elongated guide wire further comprises a fixation element for fixing the elongated guide wire to the ventricular septum.

16. The system of claim 15, wherein the fixation element of the elongated guide wire comprises a fixation helix, and the guide wire electrode is disposed proximate a distal end of the fixation helix.

17. The system of claim 12, wherein a proximal portion of the elongated guide wire extending proximally from the housing being subsequently separable from a distal portion of the elongated guide wire and withdrawn from the patient's heart.

18. The system of claim 17, wherein the wire lumen is configured to frictionally engage the elongated guide wire in order to electrically couple and mechanically secure the LCP to the elongated guide wire.

19. The system of claim 17, wherein the wire lumen includes a threaded section that is configured to engage a corresponding threaded section on the elongated guide wire in order to electrically couple and mechanically secure the LCP to the elongated guide wire.

20. A trans-septal implantable medical device (IMD) system configured for deployment within a patient's heart, adjacent a septum within the patient's heart, for pacing and/or sensing a patient's heart, the trans-septal IMD system comprising:
- a guide wire that includes a guide wire electrode disposed at or near a distal end of the guide wire;
- a housing configured to be positioned adjacent a first side of the septum and not extending through the septum once the trans-septal IMD is implanted;
- a power source disposed within the housing;
- circuitry disposed within the housing and operably coupled to the power source;
- a first electrode disposed relative to the housing and positioned to contact the first side of the septum once implanted;
- a second electrode configured to be spaced away from the housing and into or through the septum once the trans-septal IMD is implanted, the second electrode comprising the guide wire electrode disposed at or near a distal end of the elongated guide wire;
- the circuitry configured to pace the patient's heart and/or sense electrical activity of the patient's heart via the first electrode and the second electrode;
- the housing defining a wire lumen that is configured to permit the trans-septal IMD to be delivered to a position proximate the septum over the elongated guide wire; and
- a fixation element operable to fixate the trans-septal IMD relative to the septum.

* * * * *